(12) United States Patent
Kramer et al.

(10) Patent No.: US 7,402,639 B2
(45) Date of Patent: *Jul. 22, 2008

(54) 1-ALKOXY-POLYALKYL-PIPERIDINE DERIVATIVES AND THEIR USE AS POLYMERIZATION REGULATORS

(75) Inventors: Andreas Kramer, Düdingen (CH); Peter Nesvadba, Marly (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 571 days.

This patent is subject to a terminal disclaimer.

(21) Appl. No.: 11/035,915

(22) Filed: Jan. 14, 2005

(65) Prior Publication Data

US 2005/0131177 A1 Jun. 16, 2005

Related U.S. Application Data

(62) Division of application No. 10/422,497, filed on Apr. 24, 2003, now Pat. No. 6,927,295, which is a division of application No. 10/013,884, filed on Dec. 11, 2001, now Pat. No. 6,683,142, which is a division of application No. 09/262,804, filed on Mar. 4, 1999, now Pat. No. 6,353,107.

(30) Foreign Application Priority Data

Mar. 9, 1998 (EP) ................... 98810194
Jun. 11, 1998 (EP) ................... 98810531

(51) Int. Cl.
 *C08F 2/38* (2006.01)
 *C08F 2/50* (2006.01)
 *C08F 4/00* (2006.01)
(52) U.S. Cl. ............... 526/204; 522/9; 252/183.11; 546/220
(58) Field of Classification Search ............ 526/204; 522/9; 252/183.11; 546/220
See application file for complete search history.

(56) References Cited

U.S. PATENT DOCUMENTS 3,975,357 A 8/1976 Murayama et al. ......... 524/99

(Continued)

FOREIGN PATENT DOCUMENTS

CA 2173703 10/1996

(Continued)

OTHER PUBLICATIONS

Hawker et al., Macromolecules, 1996, 29, pp. 2686-2688.
Hawker, Angew. Chem., 1995, 107, pp. 1623-1627.

(Continued)

*Primary Examiner*—Celia Chang
(74) *Attorney, Agent, or Firm*—Tyler A. Stevenson

(57) ABSTRACT

The present invention relates to 1-alkoxy-polyalkyl-peridine derivatives containing a structural element of formula (I)

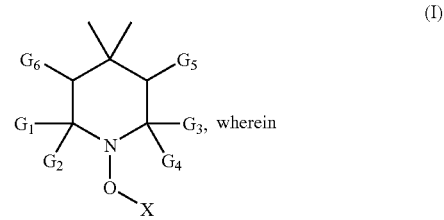

(I)

$G_1, G_2, G_3, G_4$ are independently $C_1$-$C_6$alkyl with the proviso that at least one is not methyl or $G_1$ and $G_2$ or $G_3$ and $G_4$, or $G_1$ and $G_2$ and $G_3$ and $G_4$ together form a $C_5$-$C_{12}$cycloalkyl group;

$G_5$, $G_6$ independently are H, $C_1$-$C_{18}$alkyl, phenyl, naphthyl or a group COO$C_1$-$C_{18}$alkyl and X represents a group such that the free radical X• derived from X is capable of initiating polymerization of ethylenically unsaturated monomers, with the proviso that compounds A1 and A2 are excluded

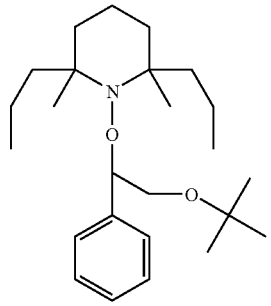

(A1)

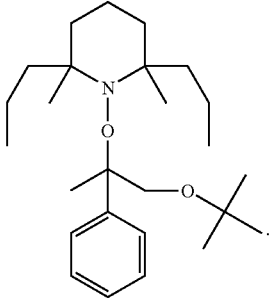

(A2)

Further subjects of the invention are a polymerizable composition comprising a) at least one ethylenically unsaturated monomer and b) a 1-alkoxy-polyalkyl-piperidine derivative, a process for polymerizing ethylenically unsaturated monomers, and the use of 1-alkoxy-polyalkyl-piperidine derivatives for controlled polymerization. The intermediate N-oxyl derivatives, a composition of the N-oxyl derivatives with ethylenically unsaturated monomers and a free radical initiator X•, as well as a process for polymerization are also subjects of the present invention.

2 Claims, No Drawings

U.S. PATENT DOCUMENTS

| | | | | |
|---|---|---|---|---|
| 4,141,883 | A | 2/1979 | Soma et al. | 524/82 |
| 4,581,429 | A | 4/1986 | Solomon et al. | 526/220 |
| 5,457,204 | A | 10/1995 | Steinmann | 546/242 |
| 5,721,320 | A | 2/1998 | Priddy et al. | 525/316 |
| 6,525,151 | B1 | 2/2003 | Roth et al. | 526/220 |
| 6,683,142 | B2* | 1/2004 | Kramer et al. | 526/204 |
| 6,891,008 | B2* | 5/2005 | Nesvadba et al. | 526/204 |
| 7,160,966 | B2* | 1/2007 | Nesvadba et al. | 526/204 |

FOREIGN PATENT DOCUMENTS

| | | |
|---|---|---|
| CA | 2213526 | 2/1998 |
| EP | 0135280 | 3/1985 |
| EP | 0155912 | 9/1985 |
| EP | 0512951 | 11/1992 |
| EP | 0638617 | 2/1995 |
| EP | 0735052 | 10/1996 |
| EP | 0792911 | 9/1997 |
| GB | 1 496 454 | 12/1977 |
| GB | 1 496 844 | 1/1978 |
| NL | 1011394 | 8/1999 |
| WO | 97/36894 | 10/1997 |
| WO | 97/36944 | 10/1997 |
| WO | 98/13392 | 4/1998 |
| WO | 98/30601 | 7/1998 |
| WO | 98/44008 | 10/1998 |
| WO | 99/03894 | 1/1999 |
| WO | 99/46261 | 9/1999 |

OTHER PUBLICATIONS

Connolly et al., Tetrahedron Letters, vol. 37, No. 28, pp. 4919-4922, (1996).
Hawker et al., Macromol. Chem. Phys., 198, pp. 155-166 (1997).
Abstract for EP 0638617 (1995).
E. Malström et al., Tetrahedron, vol. 53, No. 45, pp. 15225-15236 (1997).
I. Li et al., Macromolecules, (1995), vol. 28, pp. 6692-6693.
S. Kobatake et al., Macromolecules, (1997), vol. 30, pp. 4238-4240.
B. A. Howell et al., Polymer Bulletin, vol. 37, pp. 451-456 (1996).
T. Connolly et al., Tetrahedron Letters, vol. 37, No. 28, pp. 4919-4922, (1996).
G. Moad et al., Macromolecules, (1995), vol. 28, pp. 8722-8728.
C. Hawker., TRIP, vol. 4, No. 6, (1996), pp. 183-188.
C. Hawker et al., Macromolecules, vol. 29, No. 16, (1996) pp. 5245-5254.
Abstract for EP 0155912, Publication Date Sep. 25, 1985.
Chemical Abstract 79:105051 for Lee et al., Hwahak Konghak (1973), 11(1), pp. 15-22.
Chemical Abstract 72:12577 for JP 44012142 (1969).
Chemical Abstract 136:386580 for WO 02/038632 (2002).
Chemical Abstract 136:279850 for WO 02/024761 (2002).

* cited by examiner

1-ALKOXY-POLYALKYL-PIPERIDINE DERIVATIVES AND THEIR USE AS POLYMERIZATION REGULATORS

This is a divisional of application Ser. No. 10/422,497, filed Apr. 24, 2003, now U.S. Pat. No. 6,927,295, which is a divisional of application Ser. No. 10/013,884, filed Dec. 11, 2001, now U.S. Pat. No. 6,683,142, which is a divisional of application Ser. No. 09/262,804, filed Mar. 4, 1999, now U.S. Pat. No. 6,353,107.

The present invention relates to 1-alkoxy-polyalkyl-piperidine derivatives, a polymerizable composition comprising a).at least one ethylenically unsaturated monomer and b) a 1-alkoxy-polyalkyl-piperidine derivative. Further aspects of the present Invention are a process for polymerizing ethylenically unsaturated monomers, and the use of 1-alkoxy-polyalkyl-piperidine derivatives for controlled polymerization. The intermediate N-oxyl derivatives, a composition of the N-oxyl derivatives with ethylenically unsaturated monomers and a free radical initiator X•, as well as a process for polymerization are also subjects of the present invention.

The compounds of the present invention provide polymeric resin products having low polydispersity. The polymerization process proceeds with enhanced monomer to polymer conversion efficiency. In particular this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

Polymers or copolymers prepared by free radical polymerization processes inherently have broad molecular weight distributions or polydispersities which are generally higher than about four. One reason for this is that most of the free radical initiators have half lives that are relatively long, ranging from several minutes to many hours, and thus the polymeric chains are not all initiated at the same time and the initiators provide growing chains of various lengths at any time during the polymerization process. Another reason is that the propagating chains In a free radical process can react with each other in processes known as combination and disproportionation, both of which are irreversibly chain-terminating reaction processes. In doing so, chains of varying lengths are terminated at different times during the reaction process, resulting in resins consisting of polymeric chains which vary widely in length from very small to very large and which thus have broad polydispersities. If a free radical polymerization process is to be used for producing narrow molecular weight distributions, then all polymer chains must be initiated at about the same time and termination of the growing polymer-chains by combination or disproportionation processes must be avoided.

Conventional radical polymerization reaction processes pose various significant problems, such as difficulties in predicting or controlling the molecular weight, the polydispersity and the modality of the polymers produced. These prior art polymerization processes produce polymers having broad polydispersities and in some instances, low polymerization rates. Furthermore, free radical polymerization processes in bulk of the prior art are difficult to control because the polymerization reaction is strongly exothermic and an efficient heat removal in the highly viscous polymer is mostly impossible. The exothermic nature of the prior art free radical polymerization processes often severely restricts the concentration of reactants or the reactor size upon scale-up.

Due to the above mentioned uncontrollable polymerization reactions, gel formation in conventional free radical polymerization processes are also possible and cause broad molecular weight distributions and/or difficulties during filtering, drying and manipulating the product resin.

U.S. Pat. No. 4,581,429 to Solomon et al. issued Apr. 8, 1986, discloses a free radical polymerization process which controls the growth of polymer chains to produce short chain or oligomeric homopolymers and copolymers, Including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O• groups are derived from 1,1,3,3 tetraethyilsoindoline, 1,1,3,3 tetrapropylisoindoline, 2,2,6,6 tetrarmethylpiperidine, 2,2,5,5 tetramethylpyrrolidine or di-t-butylamine. However, the suggested compounds do not fulfill all requirements. Particularly the polymerization of acrylates does not proceed fast enough and/or the monomer to polymer conversion is not as high as desired.

Recently other attempts to develop new polymerization regulators have been published. WO 98/4408 and WO 98/30601 disclose heterocyclic compounds suitable for controlled polymerization processes. WO 98/13392 discloses open chain alkoxyamines which are derived from NO gas or from nitroso compounds.

EP-A-735 052 discloses a method for preparing thermoplastic polymers of narrow polydispersities by free radical-initiated polymerization, which comprises aciding a free radical initiator and a stable free radical agent to the monomer compound.

This method has the disadvantage that uncontrollable recombinations of initiator radicals may occur immediately after their formation, thus producing variable ratios between initiator radicals and stable free radicals. Consequently in some cases there is no good control of the polymerization process.

There is therefore still a need for polymerization processes for the preparation of narrow polydispersity polymeric resins with defined molecular weights using the economical free radical polymerization techniques. These polymerization processes will also control the physical properties of the polymers such as viscosity, hardness, gel content, processability, clarity, high gloss, durability, and the like.

The polymerization processes and resin products of the present invention are useful in many applications, including a variety of specialty applications, such as for the preparation of block copolymers which are useful as compatibilizing agents for polymer blends, or dispersing agents for coating systems or for the preparation of narrow molecular weight resins or oligomers for use in coating technologies and thermoplastic films or as toner resins and liquid immersion development ink resins or ink aciditives used for electrophotographic imaging processes.

Surprisingly, it has now been found that it is possible to overcome the afore mentioned shortcomings of the prior art by providing a polymerizable composition containing specific initiator compounds. Polymerization of the composition results in a polymer or copolymer of narrow polydispersity and a high monomer to polymer conversion even at relatively low temperatures and at short reaction times, making the polymerization process particularly suitable for industrial applications. The resulting copolymers are of high purity and in many cases colorless, therefore not requiring any further purification.

One object of the present invention is to provide a 1-alkoxy-polyalkyl-piperidine derivative containing a structural element of formula (I)

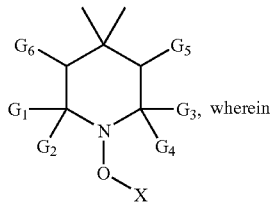

(I)

$G_1, G_2, G_3, G_4$ are independently $C_1$-$C_6$ alkyl with the proviso that at least one is not methyl or $G_1$ and $G_2$ or $G_3$ and $G_4$, or $G_1$ and $G_2$ and $G_3$ and $G_4$ together form a $C_5$-$C_{12}$ cycloalkyl group;

$G_5, G_6$ independently are H, $C_1$-$C_{18}$ alkyl, phenyl, naphthyl or a group $COOC_1$-$C_{18}$ alkyl and X represents a group having at least one carbon atom and is such that the free radical X• derived from X is capable of initiating polymerization of ethylenically unsaturated monomers, with the proviso that compounds A1 and A2 are excluded

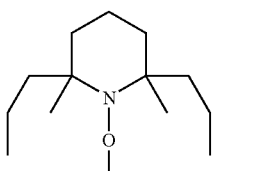

(A1)

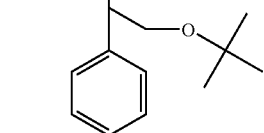

(A2)

The alkyl radicals in the various substituents may be linear or branched. Examples of alkyl containing 1 to 18 carbon atoms are methyl, ethyl, propyl, isopropyl, butyl, 2butyl, isobutyl, t-butyl, pentyl, 2-pentyl, hexyl, heptyl, octyl, 2-ethylhexyl, t-octyl, nonyl, decyl undecyl, dodecyl, tridecyl, tetradecyl, hexadecyl and octadecyl.

$C_5$-$C_{12}$ cycloalkyl is typically, cyclopentyl, methylcyclopentyl, dimethylcyclopentyl, cyclohexyl, methylcyclohexyl.

Preferred compounds or mixture of compounds are any of formulae A to S.

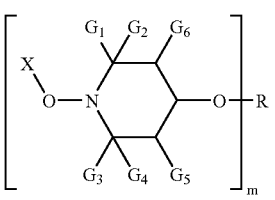

(A)

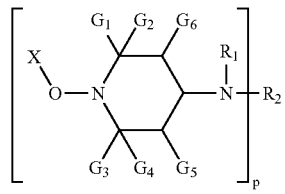

(B)

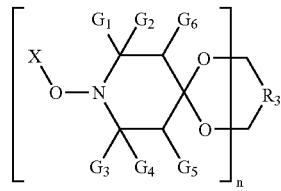

(C)

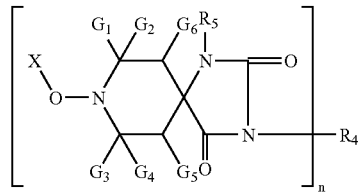

(D)

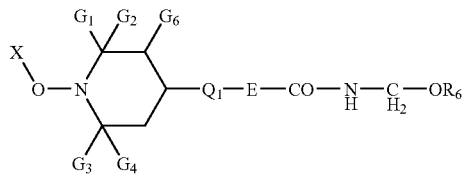

(E)

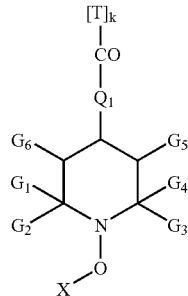

(F)

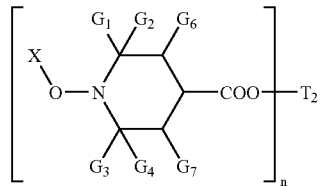

(G)

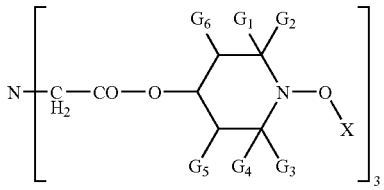

(H)

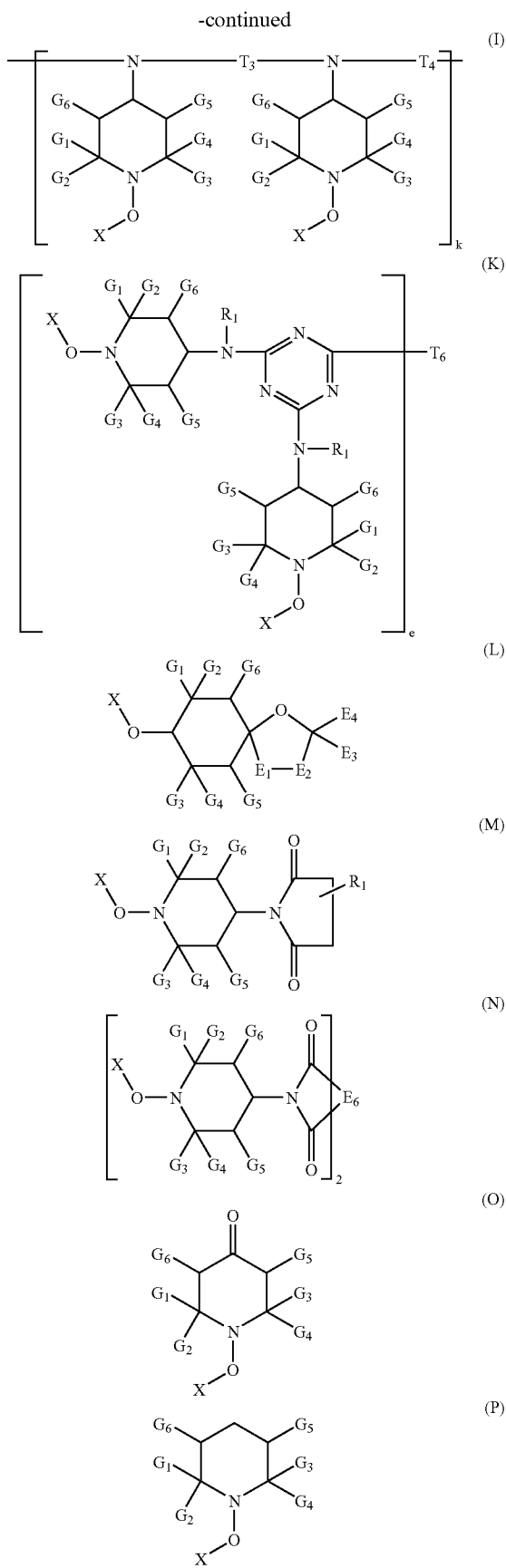

wherein
G₁, G₂, G₃ and G₄ are independently alkyl of 1 to 4 carbon atoms, or G₁ and G₂ together and G₃ and G₄ together, or G₁ and G₂ together or G₃ and G₄ together are pentamethylene;
G₅, and G₆ are independently hydrogen or $C_1$-$C_4$ alkyl;
R, if m is 1, is hydrogen, $C_1$-$C_{18}$alkyl which is uninterrupted or $C_2$-$C_{18}$alkyl which is interrupted by one or more oxygen atoms, cyanoethyl, benzoyl, glycidyl, a monovalent radical of an aliphatic carboxylic acid having 2 to 18 carbon atoms, of a cycloaliphatic carboxylic acid having 7 to 15 carbon atoms, or an α,β-unsaturated carboxylic acid having 3 to 5 carbon atoms or of an aromatic carboxylic acid having 7 to 15 carbon atoms, where each carboxylic acid can be substituted in the aliphatic, cycloaliphatic or aromatic moiety by 1 to 3 —COOZ₁₂ groups, in which $Z_{12}$ is H, $C_1$-$C_{20}$alkyl, $C_3$-$C_{12}$alkenyl, $C_5$-$C_7$cycloalkyl, phenyl or benzyl; or
R is a monovalent radical of a carbamic acid or phosphorus-containing acid or a monovalent silyl radical;
R, if m is 2, is $C_2$-$C_{12}$alkylene, $C_4$-$C_{12}$alkenylene, xylylene, a divalent radical of an aliphatic dicarboxylic acid having 2 to 36 carbon atoms, or a cycloaliphatic or aromatic dicarboxylic acid having 8-14 carbon atoms or of an aliphatic, cycloaliphatic or aromatic dicarbamic acid having 8-14 carbon atoms, where each dicarboxylic acid may be substituted in the aliphatic, cycloaliphatic or aromatic moiety by one or two —COOZ₁₂ groups; or R is a divalent radical of a phosphorus-containing acid or a divalent silyl radical;

R, if m is 3, is a trivalent radical of an aliphatic, cycloaliphatic or aromatic tricarboxylic acid, which may be substituted in the aliphatic, cycloaliphatic or aromatic moiety by —COOZ$_{12}$, of an aromatic tricarbamic acid or of a phosphorus-containing acid, or is a trivalent silyl radical, R, if m is 4, is a tetravalent radical of an aliphatic, cycloaliphatic or aromatic tetracarboxylic acid;

p is 1, 2 or 3,

R$_1$ is C$_1$-C$_{12}$alkyl, C$_5$-C$_7$cycloalkyl, C$_7$-C$_8$aralkyl, C$_2$-C$_{18}$alkenoyl, C$_3$-C$_5$alkenoyl or benzoyl;

when p is 1,

R$_2$ is C$_1$-C$_{18}$alkyl, C$_5$-C$_7$cycloalkyl, C$_2$-C$_8$alkenyl unsubstituted or substituted by a cyano, carbonyl or carbamide group, or is glycidyl, a group of the formula —CH$_2$CH(OH)-Z or of the formula —CO-Z- or —CONH-Z wherein Z is hydrogen, methyl. or phenyl; or when p is 2, R$_2$ is C$_2$-C$_{12}$alkylene, C$_8$-C$_{12}$arylene, xylylene, a —CH$_2$CH(OH)CH$_2$—O—B—O—CH$_2$CH(OH)CH$_2$— group, wherein B is C$_2$-$_{10}$alkylene, C$_6$-C$_{15}$arylene or C$_6$-C$_{12}$cycloalkylene; or, provided that R$_1$ is not alkenoyl, alkenoyl or benzoyl, R$_2$ can also be a divalent acyl radical of an aliphatic, cycloaliphatic or aromatic dicarboxylic acid or dicarbamic acid, or can be the group —CO—; or R$_1$ and R$_2$ together when p is 1 can be the cyclic acyl radical of an aliphatic or aromatic 1,2- or 1,3-dicarboxylic acid; or R$_2$ is a group

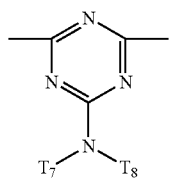

where T$_7$ and T$_8$ are independently hydrogen, alkyl of 1 to 18 carbon atoms, or T$_7$ and T$_8$ together are alkylene of 4 to 6 carbon atoms or 3-oxapentamethylene;

when p is 3,

R$_2$ is 2,4,6-triazinyl;

when n is 1,

R$_3$ is C$_2$-C$_8$-alkylene or hydroxyalkylene or C$_4$-C$_{22}$acyloxyalkylene; or when n is 2, R$_3$ is (—CH$_2$)$_2$C(CH$_2$—)$_2$;

when n is 1,

R$_4$ is hydrogen, C$_1$-C$_{12}$alkyl, C$_3$-C$_5$alkenyl, C$_7$-C$_9$aralkyl, C$_5$-C$_7$cycloalkyl, C$_2$-C$_4$hydroxyalkyl, C$_2$-C$_6$alkoxyalkyl, C$_6$-C$_{10}$aryl, glycidyl, a group of formula —(CH$_2$)$_m$—COO-Q or of the formula —(CH$_2$)$_m$—O—CO-Q wherein m is 1 or 2 and Q is C$_1$-C$_4$alkyl or phenyl; or when n is 2, R$_4$ is C$_2$-C$_{12}$alkylene, C$_6$-C$_{12}$arylene, a group —CH$_2$CH(OH)CH$_2$—O—D—O—CH$_2$(OH)CH$_2$— wherein D is C$_2$-C$_{10}$alkylene, C$_6$-C$_{15}$arylene or C$_6$-C$_{12}$cycloalkylene, or a group —CH$_2$CH(OZ$_1$)CH$_2$—(OCH$_2$CH(OZ$_1$)CH$_2$)$_2$— wherein Z$_1$ is hydrogen, C$_1$-C$_{18}$alkyl, allyl, benzyl, C$_2$-C$_{12}$alkanoyl or benzoyl;

R$_5$ is hydrogen, C$_1$-C$_{12}$alkyl, allyl, benzyl, glycidyl or C$_2$-C$_6$alkoxyalkyl;

Q$_1$ is —N(R$_7$)— or —O—;

E is C$_1$-C$_3$alkylene, the group —CH$_2$CH(R$_8$)—O— wherein R$_8$ is hydrogen, methyl or phenyl, the group —(CH$_2$)$_3$—NH— or a direct bond;

R$_7$ is C$_1$-C$_{18}$alkyl, C$_5$-C$_7$-cycloalkyl, C$_7$-C$_{12}$aralkyl, cyanoethyl, C$_6$-C$_{10}$-aryl, the group —CH$_2$CH(R$_8$)—OH; or a group of the formula

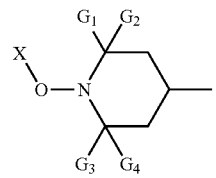

or a group of the formula

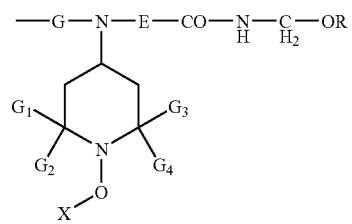

wherein G is C$_2$-C$_6$alkylene or C$_6$-C$_{12}$arylene and R is as defined above; or R$_7$ is a group -E-CO—NH—CH$_2$—OR$_6$;

R$_6$ is hydrogen or C$_1$-C$_{18}$alkyl;

Formula (F) denotes a recurring structural unit of a oligomer where T is ethylene or 1,2-propylene, or is a repeating structural unit derived from an α-olefin copolymer with an alkyl acrylate or methacrylate;

k is 2 to 100;

R$_{10}$ is hydrogen, C$_1$-C$_{12}$alkyl or C$_1$-C$_{12}$alkoxy;

T$_2$ has the same meaning as R4;

T$_3$ and T$_4$ are independently alkylene of 2 to 12 carbon atoms, or T$_4$ is a group

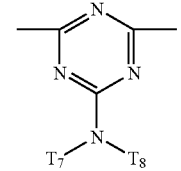

T$_5$ is C$_2$-C$_{22}$alkylene, C$_5$-C$_7$cycloalkylene, C$_1$-C$_4$alkylenedi(C$_5$-C$_7$cycloalkylene), phenylene or phenylenedi(C$_1$-C$_4$alkylene);

T$_6$ is

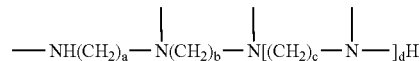

where a, b and c are independently 2 or 3, and d is 0 or 1;

e is 3 or 4;

T$_7$ and T$_8$ are independently hydrogen C$_1$-C$_{18}$alkyl, or T$_7$ and T$_8$ together are C$_4$-C$_6$alkylene or 3-oxapenthamethylene;

$E_1$ and $E_2$, being different, each are —CO— or —N($E_5$)—, where $E_5$ is hydrogen, $C_1$-$C_{12}$alkyl or $C_4$-$C_{22}$alkoxycarbonylalkyl;

$E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms;

$E_4$ is hydrogen, alkyl of 1 to 30 carbon atoms, phenyl, naphthyl or phenylalkyl of 7 to 12 carbon atoms; or $E_3$ and $E_4$ together are polymethylene of 4 to 17 carbon atoms, or said polymethylene substituted by up to four alkyl groups of 1 to 4 carbon atoms; and $E_6$ is an aliphatic or aromatic tetravalent radical.

$C_3$-$C_{12}$alkenyl is for example propenyl, butenyl, pentenyl, hexenyl, heptenyl, octenyl, dodecenyl including their isomers.

$C_7$-$C_9$aralkyl is for example benzyl, phenylpropyl, α,α-dimethylbenzyl or α-methylbenzyl.

$C_2$-$C_{18}$alkyl interrupted by at least one O atom is for example —CH$_2$—CH$_2$—O—CH$_2$—CH$_3$, —CH$_2$—CH$_2$—O—CH$_3$ or —CH$_2$—CH$_2$—O—CH$_2$—CH$_2$—O—CH$_2$—CH$_3$. It is preferably derived from polyethlene glycol. A general description is —((CH$_2$)$_a$—O)$_b$—H/CH$_3$, wherein a is a number from 1 to 6 and b is a number from 2 to 10.

If R is a monovalent radical of a carboxylic acid, it is, for example, an acetl, caproyl, stearoyl, acryloyl, methacryloyl, benzoyl or β-(3,5-di-tert-butyl-4-hydroxyphenyl)propionyl radical.

If R is a monovalent silyl radical, it is, for example, a radical of the formula —(C$_j$H$_{2j}$)—Si(Z')$_2$Z", in which j is an integer in the range from 2 to 5, and Z' and Z", independently of one another, are $C_1$-$C_4$alkyl or $C_1$-$C_4$alkoxy.

If R is a divalent radical of a dicarboxylic acid, it is, for example, a malonyl, succinyl, glutaryl, adipoyl, suberoyl, sebacoyl, maleoyl, itaconyl, phthaloyl, dibutylmalonyl, dibenzylmalonyl, butyl(3,5-di-tert-butyl-4-hydroxybenzyl) malonyl or bicycloheptenedicarbonyl radical or a group of the formula

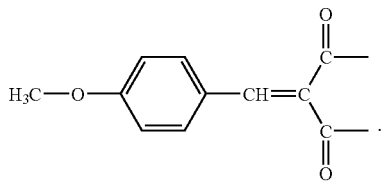

If R is a trivalent radical of a tricarboxylic acid, it is, for example, a trimellitoyl, citryl or nitrilotriacetyl radical.

If R is a tetravalent radical of a tetracarboxylic acid, it is, for example, the tetravalent radical of butane-1,2,3,4-tetracarboxylic acid or of pyromellitic acid.

If R is a divalent radical of a dicarbamic acid, it is, for example, hexamethylenedicarbamoyl or 2,4-toluylenedicarbamoyl radical.

$C_1$-$C_{18}$alkanoyl is for example, formyl, propionyl, butyryl, octanoyl, dodecanoyl but preferably acetyl and $C_3$-$C_5$alkenoyl is in particular acryloyl.

Any $C_2$-$C_{12}$alkylene radicals are, for example, ethylene, propylene, 2,2-dimethylpropylene, tetramethylene, hexamethylene, octamethylene, decamethylene or dodecamethylene.

Any $C_6$-$C_{15}$arylene substituents are, for example, o-, m- or p-phenylene, 1,4-naphthylene or 4,4'-diphenylene.

$C_6$-$C_{12}$cycloalkylene is, in particular, cyclohexylene.

Hydroxyl-, cyano-, alkoxycarbonyl- or carbamide-substituted $C_1$-$C_4$alkyl can be, for example, 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl)ethyl.

Any $C_2$-$C_6$alkoxyalkyl substituents are, for example, methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

Preferably $G_6$ is hydrogen and $G_5$ is hydrogen or $C_1$-$C_4$alkyl.

Preferably $G_1$, $G_2$, $G_3$ and $G_4$ are independently $C_1$-$C_4$alkyl, with the proviso that at least one is different from methyl.

More preferred $G_1$ and $G_3$ are methyl and $G_2$ and $G_4$ are ethyl or propyl.

In another preferred group of compounds $G_1$ and $G_2$ are methyl and $G_3$ and $G_4$ are ethyl or propyl.

Preferably X is selected from the group consisting of —CH$_2$-aryl,

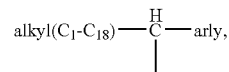

—CH$_2$—CH$_2$-aryl,

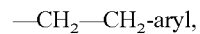

($C_5$-$C_6$cycloalkyl)$_2$CCN, ($C_1$-$C_{12}$alkyl)$_2$CCN, —CH$_2$CH=CH$_2$, ($C_1$-$C_{12}$)alkyl-CR$_{20}$-C(O)—$C_1$-$C_{12}$) alkyl, ($C_1$-$C_{12}$)alkyl-CR$_{20}$-C(O)—($C_6$-$C_{10}$)aryl, ($C_1$-$C_{12}$) alkyl-CR$_{20}$-C(O)—($C_1$-$C_{12}$)alkoxy, ($C_1$-$C_{12}$)alkyl-CR$_{20}$-C (O)-phenoxy, ($C_1$-$C_{12}$)alkyl-CR$_{20}$-C(O)—N-di($C_1$-$C_{12}$) alkyl, ($C_1$-$C_{12}$)alkyl-CR$_{20}$-C—NH($C_1$-$C_2$)alkyl, ($C_1$-$C_{12}$) alkyl-CR$_{20}$—CO—NH$_2$, —CH$_2$CH=CH—CH$_3$, —CH$_2$—C(CH$_3$)=CH$_2$, —CH$_2$—CH=CH-phenyl,

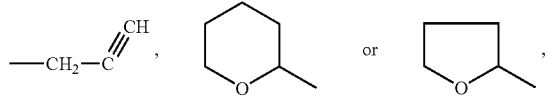

wherein $R_{20}$ is hydrogen or $C_1$-$C_{12}$alkyl;

the aryl groups are phenyl or naphthyl which are unsubstituted or substituted with $C_1$-$C_{12}$alkyl, halogen, $C_1$-$C_{12}$alkoxy, $C_1$-$C_{12}$alkylcarbonyl, glycidyloxy, OH, —COOH or —COOC$_1$-$C_{12}$alkyl.

More preferred are compounds, wherein X is selected from the group consisting of —CH$_2$-phenyl, CH$_3$CH-phenyl, (CH$_3$)$_2$C-phenyl, ($C_5$-$C_6$cycloalkyl)$_2$CCN, (CH$_3$)$_2$CCN, —CH$_2$CH=CH$_2$, CH$_3$CH—CH=CH$_2$ ($C_1$-$C_8$alkyl)CR$_{20}$-C (O)-phenyl, ($C_1$-$C_8$)alkyl-CR$_{20}$-C(O)—($C_1$-$C_8$)alkoxy, ($C_1$-$C_8$)alkyl-CR$_{20}$-C(O)—($C_1$-$C_8$)alkyl, ($C_1$-$C_8$)alkyl-CRC (O)—N-di($C_1$-$C_8$)alkyl, ($C_1$-$C_8$)alkyl-CR$_{20}$-C(O)—NH($C_1$-$C_8$)alkyl, ($C_1$-$C_8$)alkyl-CR$_{20}$-C(O)—NH$_2$, wherein $R_{20}$ is hydrogen or ($C_1$-$C_8$)alkyl.

Particularly preferred are compounds, wherein X is selected from the group consisting of —$CH_2$-phenyl, $CH_3$CH-phenyl, $(CH_3)_2$C-phenyl, $(C_5$-$C_6$cycloalkyl$)_2$CCN, $(CH_3)_2$CCN, —$CH_2$CH=$CH_2$, $CH_3$CH—CH=$CH_2$ ($C_1$-$C_4$alkyl)$CR_{20}$-C(O)-phenyl, ($C_1$-$C_4$)alkyl-$CR_{20}$-C(O)—($C_1$-$C_4$)alkoxy, ($C_1$-$C_4$)alkyl-$CR_{20}$-C(O)—($C_1$-$C_4$)alkyl, ($C_1$-$C_4$)alkyl-$CR_{20}$-C(O)—N-di($C_1$-$C_4$)alkyl, ($C_1$-$C_4$)alkyl-$CR_{20}$-C(O)—NH($C_1$-$C_4$)alkyl, ($C_1$-$C_4$)alkyl-$CR_{20}$-C(O)—$NH_2$, wherein $R_{20}$ is hydrogen or ($C_1$-$C_4$)alkyl.

In a preferred group of compounds X contains no open chain alkylether group.

Preferred compounds are those of formula A, B, O or P; particularly preferred of formula A, B or O and more preferred of formula A or B, wherein the substituents have the meanings as defined before.

A preferred group of compounds are those of formula A, B or O, wherein
m is 1,
R is hydrogen, $C_1$-$C_{18}$alkyl which is uninterrupted or interrupted by one or more oxygen atoms, cyanoethyl, benzoyl, glycidyl, a monovalent radical of an aliphatic carboxylic acid having 2 to 18 carbon atoms, of a cycloaliphatic carboxylic acid having 7 to 15 carbon atoms, or an α,β-unsaturated carboxylic acid having 3 to 5 carbon atoms or of an aromatic carboxylic acid having 7 to 15 carbon atoms;
p is 1;
$R_1$ is $C_1$-$C_{12}$alkyl, $C_5$-$C_7$cycloalkyl, $C_7$-$C_8$aralkyl, $C_2$-$C_{18}$alkanoyl, $C_3$-$C_5$alkenoyl or benzoyl;
$R_2$ is $C_1$-$C_{18}$alkyl, $C_5$-$C_7$cycloalkyl, $C_2$-$C_8$alkenyl unsubstituted or substituted by a cyano, carbonyl or carbamide group, or is glycidyl, a group of the formula —$CH_2$CH(OH)—Z or of the formula —CO—Z or —CONH—Z wherein Z is hydrogen, methyl or phenyl.

Amongst the group of compounds of formula A, B or O those are more preferred, wherein
R is hydrogen, $C_1$-$C_{18}$alkyl, cyanoethyl, benzoyl, glycidyl, a monovalent radical of an aliphatic, carboxylic acid;
$R_1$ is $C_1$-$C_{12}$alkyl, $C_7$-$C_8$aralkyl, $C_2$-$C_{18}$alkanoyl, $C_3$-$C_5$alkenoyl or benzoyl;
$R_2$ is $C_1$-$C_{18}$alkyl, glycidyl, a group of the formula —$CH_2$CH(OH)—Z or of the formula —CO—Z, wherein Z is hydrogen, methyl or phenyl.

A further preference for this subgroup is that $G_6$ is hydrogen and $G_5$ is hydrogen or $C_1$-$C_4$alkyl, $G_1$ and $G_3$ are methyl and $G_2$ and $G_4$ are ethyl or propyl or $G_1$ and $G_2$ are methyl and $G_3$ and $G_4$ are ethyl or propyl.

In addition for the compounds of formula A, B or O a preferred group X is selected from the group consisting of —$CH_2$-phenyl, $CH_3$CH-phenyl, $(CH_3)_2$C-phenyl, $(C_5$-$C_6$cycloalkyl$)_2$CCN, $(CH_3)_2$CCN, —$CH_2$CH=$CH_2$, $CH_3$CH—CH=$CH_2$, ($C_1$-$C_4$alkyl)$CR_{20}$-C(O)-phenyl, ($C_1$-$C_4$)alkyl-$CR_{20}$-C(O)—($C_1$-$C_4$)alkoxy, ($C_1$-$C_4$)alkyl-$CR_{20}$-C(O)—($C_1$-$C_4$)alkyl, ($C_1$-$C_4$)alkyl-$CR_{20}$-C(O)—N-di($C_1$-$C_4$)alkyl, ($C_1$-$C_4$)alkyl-$CR_{20}$-C(O)—NH($C_1$-$C_4$)alkyl, ($C_1$-$C_4$)alkyl-$CR_{20}$-C(O)—$NH_2$, wherein $R_{20}$ is hydrogen or ($C_1$-$C_4$)alkyl.

Most preferred are the compounds of formula (A), wherein $G_5$ and $G_8$ are hydrogen or methyl, $G_1$ and $G_3$ are methyl and $G_2$ and $G_4$ are ethyl or $G_1$ and $G_2$ are methyl and $G_3$ and $G_4$ are ethyl;
m is 1; R is hydrogen, $C_1$-$C_{18}$alkyl or a group —C(O)—($C_2$-$C_{18}$)alkyl; and
X is —$CH_2$-phenyl, $CH_3$CH-phenyl, $(CH_3)_2$C-phenyl, $(C_5$-$C_6$cycloalkyl$)_2$CCN, $(CH_3)_2$CCN, —$CH_2$CH=$CH_2$, $CH_3$CH—CH=$CH_2$ ($C_1$-$C_4$alkyl)$CR_{20}$-C(O)-phenyl, ($C_1$-$C_4$)alkyl-$CR_{20}$-C(O)—($C_1$-$C_4$)alkoxy, ($C_1$-$C_4$)alkyl-$CR_{20}$-C(O)—($C_1$-$C_4$)alkyl, ($C_1$-$C_4$)alkyl-$CR_{20}$-C(O)—N-di($C_1$-$C_4$)alkyl, ($C_1$-$C_4$)alkyl-$CR_{20}$-C(O)—NH($C_1$-$C_4$)alkyl, ($C_1$-$C_4$)alkyl-$CR_2$C(O)—$NH_2$, wherein $R_{20}$ is hydrogen or ($C_1$-$C_4$)alkyl.

If R is $C_1$-$C_{18}$alkyl, propyl is particularly preferred.
If R is —C(O)—($C_2$-$C_{18}$)alkyl, —C(O)—$C_{11}H_{23}$ and —C(O)—$C_{17}H_{35}$ are particularly preferred.

A further subject of the invention is a polymerizable composition, comprising
a) at least one ethylenically unsaturated monomer or oligomer, and
b) a 1-alkoxy-polyalkyl-piperidine derivative containing a structural element of formula (I)

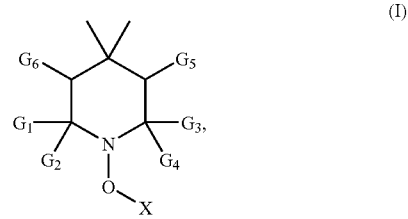

wherein
$G_1$, $G_2$, $G_3$, $G_4$ are independently $C_1$-$C_6$alkyl with the proviso that at least one is not methyl or $G_1$ and $G_2$ or $G_3$ and $G_4$, or $G_1$ and $G_2$ and $G_3$ and $G_4$ together form a $C_5$-$C_{12}$doalkyl group;
$G_5$, $G_6$ independently are H, $C_1C_{18}$alkyl, phenyl, naphthyl or a group COO$C_1$-$C_{18}$alkyl and X represents a group having at least one carbon atom and is such that the free radical X• derived from X is capable of initiating polymerization of ethylenically unsaturated monomers, with the proviso that compounds A1 and A2 are excluded

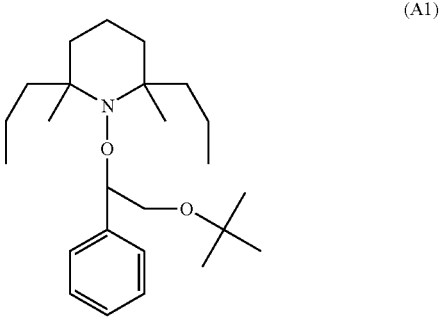

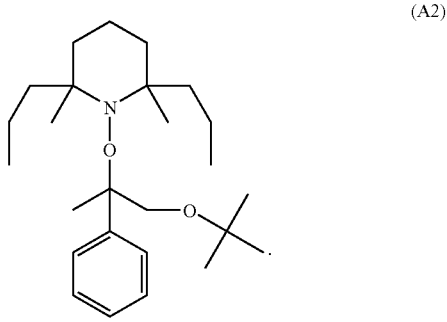

Definitions for the substituents and preferred formulas have already been given. They apply also for the composition including the preferences.

Typically the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylo-nitriles, (alkyl)acrylamides, vinyl halides or vinylidene halides.

Preferred ethylenically unsaturated monomers are ethylene, propylene, n-butylene, i-butylene, isoprene, 1,3-butadiene, $\alpha$-$C_5$-$C_{18}$alkene, styrene, $\alpha$-methyl styrene, p-methyl styrene or a compound of formula $CH_2=C(R_a)-(C=Z)-R_b$, wherein $R_a$ is hydrogen or $C_1$-$C_4$alkyl, $R_b$ is $NH_2$, $O^-(Me^+)$, glycidyl, unsubstituted $C_1$-$C_{18}$alkoxy, $C_2$-$C_{100}$alkoxy interrupted by at least one N and/or O atom, or hydroxy-substituted $C_1$-$C_{18}$alkoxy, unsubstituted $C_1$-$C_{18}$alkylamino, di($C_1$-$C_{18}$alkyl)amino, hydroxy-substituted $C_1$-$C_{18}$alkylamino or hydroxy-substituted di($C_1$-$C_{18}$alkyl)amino, $-O-CH_2-CH_2-N(CH_3)_2$ or $-O-CH_2-CH_2-N^+H(CH_3)_2$ $An^-$;

$An^-$ is a anion of a monovalent organic or inorganic acid;

Me is a monovalent metal atom or the ammonium ion.

Z is oxygen or sulfur.

Examples for $R_a$ as $C_2$-$C_{100}$alkoxy interrupted by at least one O atom are of formula

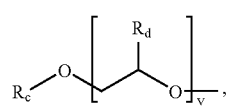

wherein $R_c$ is $C_1$-$C_{25}$alkyl, phenyl or phenyl substituted by $C_1$-$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

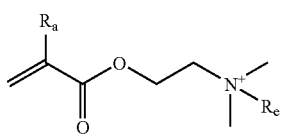

$An^-$ or

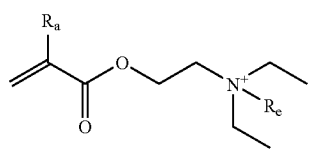

$An^-$, wherein $An^-$ and $R_a$ have the meaning as defined above and $R_e$ is methyl or benzyl. $An^-$ is preferably $Cl^-$, $Br^-$ or $^-O_3S-CH_3$.

Further acrylate monomers are

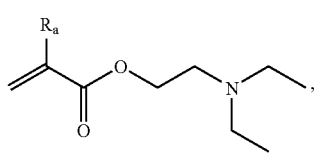

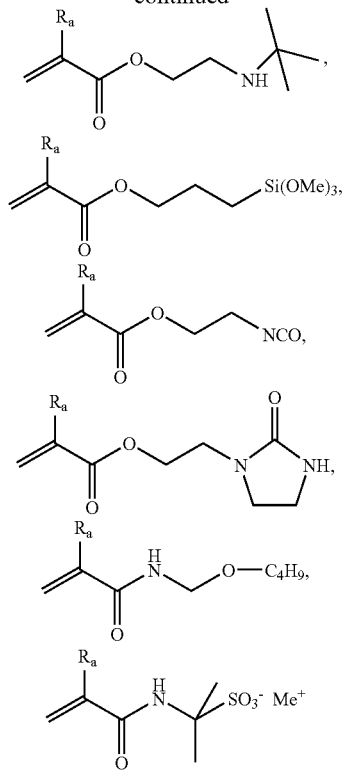

Examples for suitable monomers other than acrylates are

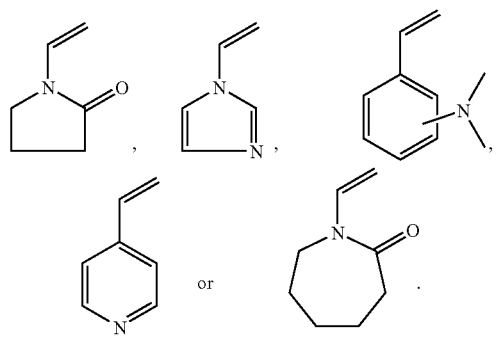

Preferably $R_a$ is hydrogen or methyl, $R_b$ is $NH_2$, gycidyl, unsubstituted or with hydroxy substituted $C_1$-$C_4$alkoxy, unsubstituted $C_1$-$C_4$alkylamino, di($C_1$-$C_4$alkyl)amino, hydroxy-substituted $C_1$-$C_4$alkylamino or hydroxy-substituted di($C_1$-$C_4$alkyl)amino; and Z is oxygen.

Particularly preferred ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl (meth)acrylate, dimethylaminoethyl(meth)acrylate, glycidyl(meth)acrylates, acrylonitrile, acrylamide, methacrylamide or dimethylaminopropyl-methacrylamide.

Preferably the initiator compound is present in an amount of from 0.01 mol-% to 30 mol-%, more preferably in an amount of from 0.1 mol-% to 20 mol-% and most preferred in an amount of from 0.5 mol-% to 10 mol-% based on the monomer or monomer mixture.

When monomer mixtures are used mol% is calculated on the average molecular weight of the mixture.

Another subject of the present invention is a process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of an initiator compound containing a structural element of formula (I) under reaction conditions capable of effecting scission of the O—C bond to form two free radicals, the radical •X being capable of Initiating polymerization.

Preferably scission of the O—C bond is effected by ultrasonic treatment, heating or exposure to electromagnetic radiation, ranging from γ to microwaves.

More preferably the scission of the O—C bond is effected by heating and takes place at a temperature of between 50° C. and 160° C.

The process may be carried out in the presence of an organic solvent or in the presence of water or. in mixtures of organic solvents and water. Aciditional cosolvents or. surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate),and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful In the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well. as derivatives thereof and mixtures thereof. Specific examples Include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically In the range of about 100:0 to about 10:90.

The process is particularly useful for the preparation of block copolymers.

Block copolymers are, for example, block copolymers of polystyrene and polyacrylate (e.g. poly(styrene-co-acrylate) or poly(styrene-co-acrylate-co-styrene). They are useful as adhesives or as compatibilizers for polymer blends or as polymer toughening agents. Poly(methylmethacrylate-co-acrylate) diblock copolymers or poly(methylacrylate-co-acrylate-co-methacrylate) triblock copolymers) are useful as dispersing agents for coating systems, as coating aciditives (e.g. Theological agents, compatibilizers, reactive diluents) or as resin component in coatings(e.g. high solid paints) Block copolymers of styrene, (meth)acrylates and/or acrylonitrile are useful for plastics, elastomers and adhesives.

Furthermore, block copolymers of this invention, wherein the blocks alternate between polar monomers and non-polar monomers, are useful In many applications as amphiphilic surfactants or dispersants for preparing highly uniform polymer blends.

The (co)polymers of the present Invention may have a number average molecular weight from 1000 to 400000 g/mol, preferably from 2000 to 250000 g/mol and, more preferably. from 2000 to 200000 g/mol. When produced In bulk the number average molecular weight may be up to 500000 (with the same minimum weights as mentioned above). The number average molecular weight may be determined by size exclusion chromatography (SEC), gel permeation chromatography (GPC), matrix assisted laser desorption/ionization mass spectrometry (MALDI-MS) or, if the initiator carries a group which can be easily distinguished from the monomer(s), by NMR spectroscopy or other conventional methods.

The polymers or copolymers of the present invention have preferably a polydispersity of from 1.0 to 2, more preferably of from 1.1 to 1.9 and most preferably from 1.2 to 1.8.

Thus, the present invention also encompasses in the synthesis novel block, multi-block, star, gradient, random, hyperbranched and dendritic copolymers, as well as graft or copolymers.

The polymers prepared by the present invention are useful for following applications:

adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerization is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be acided to form a second block on the growing polymer chain in a second polymerization step. Therefore it is possible to carry out aciditional polymerizations with the same or different monomer(s) to prepare multi-block copolymers.

Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer. In which a polyacrylonitrile or a poly(meth)-acrylate block is prepared first, then a styrene or butadiene block is attached thereto, and so on.

Furthermore, there is no linking group required for joining the different blocks of the present block copolymer. One can simply acid successive monomers to form successive blocks.

A plurality of specifically designed. polymers and copolymers are accessible by the present invention, such as star and graft (co)polymers as described, inter alia, by C. J. Hawker in Angew. Chemie, 1995, 107, pages 1623-1627, dendrimers as described by K. Matyaszewski et al. in Macromolecules 1996, Vol 29, No.12, pages 4167-4171, graft (co)polymers as described by C. J. Hawker et al. in Macromol. Chem. Phys. 198, 155-166(1997), random copolymers as described by C. J. Hawker In Macromolecules 1996, 29, 2686-2688, or diblock and triblock copolymers as described by N. A. Listigovers in Macromolecules 1996, 29, 8992-8993.

A further subject of the present invention is a polymer or oligomer, having attached at least one initiator group —X and at least one oxyamine group of formula (Ia)

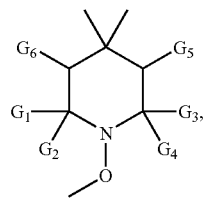

(Ia)

wherein $G_1$, $G_2$, $G_3$, $G_4$, $G_5$ and $C_6$ are as defined above, obtainable by the above described process.

The compounds of formula (I) may be prepared from the corresponding nitroxides, which are therefore intermediates for the compounds of formula (I).

Therefore still another subject of the present invention is a 1-oxy-polyalkyl-piperidine derivative containing a structural element of formula (II)

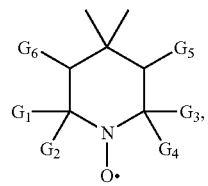

(II)

wherein
$G_1, G_2, G_3, G_4$ are independently $C_1$-$C_6$alkyl with the proviso that at least one is not methyl or $G_1$ and $G_2$ or $G_3$ and $G_4$, or $G_1$ and $G_2$ and $G_3$ and $G_4$ together form a $C_5$-$C_{12}$cycloalkyl group;
$G_5, G_6$ independently are .H, $C_1$-$C_{18}$alkyl, phenyl, naphthyl or a group $COOC_1$-$C_{18}$alkyl, with the proviso that compounds B1, B2 and B3 are excluded

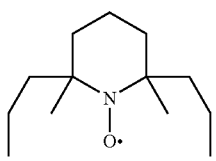

(B1)

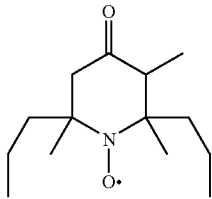

(B2)

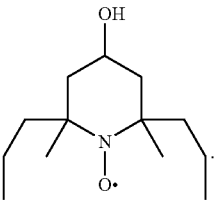

(B3)

Definitions for the substituents as well as their preferences have already been given. They apply also for the compounds of formula (II). In particular the corresponding formulas (A) to (S) and their preferred meanings are also preferred for the respective N-oxyls.

Also subject of the present invention is a polymerizable composition, comprising
a) at least one ethylenically unsaturated monomer or oligomer, and
b) a compound of formula (II) and c) a radical initiator X• capable of initiating polymerization of ethylenically unsaturated monomers.

The production of C-centered radicals X• is described, inter alia, in Houben Weyl, Methoden der Organischen Chemie, Vol. E 19a, pages 60-147. These methods can be applied in general analogy.

The source of radicals X• may be a bis-azo compound, a peroxide or a hydroperoxide.

Preferably, the source of radicals X• is 2,2'-azobisisobutyronitrile, 2,2'-azobis(2-methyl-butyronitrile), 2,2'-azobis(2, 4-dimethylvaleronitrile), 2,2'-azobis(4-methoxy-2 4dimethylvaleronitrile), 1,1'-azobis(1,1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1-bis(hydroxymethyl)ethyl]propionamide} or 2,2'-azobis{2-methyl-N-[1,1-bis(hydroxymethyl)-2-hydroxyethyl]propionamide.

Preferred peroxides and hydroperoxides are acetyl cyclohexane sulphonyl peroxide, diisopropyl peroxy dicarbonate, t-amyl perneodecanoate, t-butyl perneodecanoate, t-butyl perpivalate, t-amylperpivalate, bis(2,4-dichlorobenzoyl)peroxide, diisononanoyl peroxide, didecanoyl peroxide, dioctanoyl peroxide, dilauroyl peroxide, bis (2-methylbenzoyl) peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)3,5,5-trimethylcyclohexane, 1,1-bis(t-butylperoxy)cyclohexane, t-butyl peroxy isopropyl carbonate, t-butyl perisononaoate, 2,5-dimethylhexane 2,5.dibenzoate, t-butyl peracetate, t-amyl perbenzoate, t-butyl perbenzoate, 2,2-bis (t-butylperoxy) butane, 2,2 bis (t-butylperoxy) propane, dicumyl peroxide, 2,5-dimethylhexane- 2,5-di-t-butylperoxide, 3-t-butylperoxy 3-phenylphthalide, di-t-amyl peroxide, α,α'-bis(t-butylperoxy isopropyl) benzene, 3,5-bis (t-butylperoxy)3,5-dimethyl 1,2-dioxolane, di-t-butyl peroxide, 2,5-dimethythexyne-2,5-di-t-butylperoxide, 3,3,6,6,9,9-hexamethyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

These compounds are commercially available.

If more than one radical source is used, a mixture of substitution patterns is obtainable.

The radical source is preferably present in an amount of from 0.01 mol-% to 30 mol-%, more preferred in an amount of from 0.1 mol-% to 20 mol-% and most preferred in an amount of from 0.5 mol-% to. 10 mol-% based on the monomer or monomer mixture.

The molar ratio of the radical source to the compound of formulae II may be from 1:10 to 10:1, preferably from 1:5 to 5:1 and more preferably from 1:2 to 2:1.

Still another subject of the present invention is a process for preparing an oligomer, a cooligomer, a polymer or a copolymer (block or random) by free radical polymerization of at least one ethylenically unsaturated monomer/oligomer, which comprises subjecting the above composition to heat or actinic radiation.

Definitions and preferences for the various substituents have already been mentioned with respect to the initiator compounds. They apply also for the other subjects of the invention including the preferences.

The initiators containing a structural element of formula I may be prepared by known methods.

DE 26 21 841, U.S. Pat. No. 4,131,599 and DE 26 30 798 for example describe the preparation of 2,6-diethyl-2,3,6-trimethyl-4-oxopiperidine and 2,6-dipropyl-3-ethyl-2,6-dimethyl-4-oxo-piperidine, which are intermediates for the corresponding 1-oxo compounds.

Another method for the preparation of 2,2-dimethyl-6,6-dialkyl-4-oxopiperidine is described by F. Asinger, M. Thiel, H. Baltz, Monatshefte für Chemie 88, 464 (1957) or by J. Bobbitt et al. in J. Org. Chem. 58, 4837 (1993).

The oxidation of the piperidine compound to 1-oxo-piperidine derivatives is well known in the art and for example described by L. B. Volodarsky, V. A. Reznikov, V. I. Ovcharenko in Synthetic Chemistry of Stable Nitroxides, CRC Press, Boca Raton 1994.

The nitroxides are then transformed into the NOR compounds of formula (I) or formulae (A) to (S) respectively, according to standard methods. Examples for suitable reactions are described in T. J. Connolly, M. V. Baldovi, N. Mohtat, J. C. Scaiano.: Tet. Lett. 37, 4919 (1996), I. Li, B. A. Howell et al.: Polym. Prepr. 36, 469 (1996), K Matyjaszewski.: Macromol. Symp. 111, 47-61 (1996), P. Stipa, L. Greci, P. Carioni, E. Damiani.: Polym. Deg. Stab. 55, 323 (1997), Said Oulad Hammouch, J. M. Catala.: Macromol. Rapid Commun. 17, 149-154 (1996), Walchuk et al.: Polymer Preprints 39, 296 (1998) or Tan Ren, You-Cheng Liu, Qing-Xiang Guo.: Bull. Chem. Soc. Jpn. 69, 2935 (1996).

The compounds containing a structural element of formula (I) are useful compounds for the preparation of oligomers, cooligomers, polymers or copolymers. Hence a further subject of the invention is there use as initiators for the polymerization of ethylenically unsaturated monomers.

The following examples illustrate the invention.

A) Preparation of Compounds 2,6-diethyl-2,3,6-trimethyl-4-oxopiperidine and 2,6-dipropyl-3-ethyl-2,6-dimethyl-4-oxo-piperidine are prepared according to example 1 and 2 of DE 26 21 841.

EXAMPLE 1

2,6-diethyl-2,3,6-trimethyl-4-hydroxypiperidine

To a solution of 1182 g (0.6 mol) 2,6-diethyl-2,3,6-trimethyl-4-oxopiperidine in 1000 ml ethanol 18.2 g (0.4 mol) sodium borohydride are acided In portions and the temperature is kept below 30° C. Subsequently the solution is stirred for 2 hours at 50° C. Ethanol is distilled off, 500 ml water are acided to the residue which is subsequently extracted several times with $CH_2Cl_2$. The extract is dried over $Na_2SO_4$ and the solution is filtered. After removing the solvent 116 g (97%) 2,6-diethyl-2,3,6-trimethyl-4-hydroxypiperidine are obtained as yellowish liquid.

Elemental analysis calculated for $C_{12}H_{25}NO$: C, 72.31%; H, 12.64%; N, 7.03%. Found: C, 71.44%; H, 12.71%; N, 6.87%.

EXAMPLE 2

2,6-diethyl-2,3,6-trimethyl-4-hydroxypiperidine-1-oxyl

To a solution of 25.7 g (0.13 mol) 2,6-diethyl-2,3,6-trimethyl-4-hydroxypiperidine of example 1 in 120 ml tetrahydrofurane a solution of a solution of 54.5 g (0.22 mol) m-chlor-perbenzoic acid (70%) in 230 ml tetrahydrofurane is droppwise acided under stirring within 2 hours at 0° C. The red to brown solution is stirred over night at room temperature and 500 ml hexane, are acided. The solution is neutralized by shaking several times with 1 N $NaHCO_3$ and finally with water. The solvent is evaporated and 27.0 g (97%) 2,6-diethyl-2,3,6-trimethyl-4-hydroxypiperidine-1-oxyl are obtained as red liquid.

Elemental analysis calculated for $C_{12}H_{24}NO_2$: C, 67.25%; H, 11.29%; N, 6.54%. Found: C, 67.10%; H, 11.42%; N, 6.68%.

EXAMPLE 3

2,6-diethyl-2,3,6-trimethyl-4-oxypiperidine-1-oxyl 2,6-diethyl-2.3,6-trimethyl-4-oxopiperidine is prepared in analogy to example 2 by oxidizing 16 g (0.08 mol) 2,6-diethyl-2,3,6-trimethyl-4-oxopiperidine with m-chlor-perbenzoic acid. 1 g 2,6-diethyl-2,3,6-trimethyl-4-oxypiperidine-1-oxyl are obtained as red liquid.

Elemental analysis calculated for $C_{12}H_{22}NO_2$: C, 67.89%; H, 10.44%; N, 6.60%. Found: C, 68.00%; H, 10.42%; N, 6.61%.

EXAMPLE 4

2,6-diethyl-2,3,6-trimethyl-4-propyloxypiperidine-1-oxyl

In a 200 ml three neck bottle 25.6 g (0.12 mol 2,6-diethyl-2,3,6-trimethyl-4-hydroxy-piperidine-1-oxyl, 169 g (0.4 mol) sodium hydroxide, 3.86 g (0.012 mol) tetrabutyl-ammonium-bromide, 16 g water and 30 ml toluene are acided. The dear emulsion is heated up to 60° C. and within 1 h 22.1 g (0.18 mol) propylbromide are dropwise acided under stirring. The temperature is maintained for 12 h under stirring. The reaction mixture is cooled to room temperature, the water phase is separated and the organic phase is washed neutral with water and dried over $Na_2SO_4$. The organic solvent is evaporated and the residue is distilled over a short column. 21 (68%) 2,6-diethyl-2,3,6-trimethyl-4-propyloxy-piperidine-1-oxyl are obtained as red liquid.

Elemental analysis calculated for $C_{15}H_{30}NO_2$: C 70.27%; H 11.79%; N 5.46%. Found: C 70,26%; H 11.90%; N 5.34%.

EXAMPLE 5

2,6-dipropyl-2-ethyl-2,6-dimethyl-4-oxypiperidine-1-oxyl

The title compound is prepared in analogy to example 2.5 g (0.021 mol) 2,6-Dipropyl-2-ethyl-2,6-dimethyl-4-oxopiperidine are oxidized with m-chlor-perbenzoic acid. 5.5 g 2,6-dipropyl-2-ethyl-2,6-dimethyl-4-oxypiperidine-1-oxyl are obtained as red liquid.

Elemental analysis calculated for $C_{15}H_{30}NO_2$: C, 70.27%; H, 11.79%; N, 5.46%. Found: C, 72.31%; H, 11.02%; N, 5.070%.

BSP. 6

1-Benzyloxy-2,6-diethyl-2,3,6-trimethyl-4-oxypiperidine (No. 101)

In a reactor suitable for conducting photo reactions 150 ml toluene, 4.4 g (0.02 mol) 2,6-diethyl-2,3,6-trimethyl-4-oxypiperidine-1-oxyl and 12.7 g (0.087 mol) t-butylperoxide are acided. The red solution is purged with nitrogen and subsequently irradiated with a mercury immersion lamp under nitrogen at 20-25° C. After 8 h the solution is colorless. The reaction mixture is concentrated and the residue is subjected to column chromatography (silicagel, hexane-ethylacetate (9:1)). 4.8 g (77%) 1-benzyloxy-2,6-:diethyl-2,3,6-trimethyl-4-oxypiperidine are isolated as yellowish liquid.

Elemental analysis calculated for $C_{19}H_{29}NO_2$: C, 75.20%; H, 9.63%; N, 4.61%. Found: C, 75.53%; H, 9.60%; N, 4.59%.

EXAMPLE 7

1-(1-phenylethoxy)-2,6-diethyl-2,3,6-trimethyl-4-hydroxypiperidine (No. 102)

The title compound is prepared in analogy to example 6. 8.5 g (0.04 mol) 2,6-diethyl-2,3,6-trimethyl-4-hydroxypiperidine-1-oxyl are reacted with t-butylperoxide in ethylbenzene. 10.5 g (82%) 1-(1-phenylethoxy)-2,6-diethyl-2,3,6-trimethyl-4-hydroxypiperidine are obtained as yellowish liquid.

Elemental analysis calculated for $C_{20}H_{33}NO_2$: C, 75.43%; H, 10.30%; N, 4.35%. Found: C, 75.54%; H, 10.36%; N, 4.40%.

EXAMPLE 8

1-(1-phenylethoxy)-2,6-diethyl-2,3,6-trimethyl-4-propyloxypiperidine (No. 103)

The title compound is prepared in analogy to example 6. 5.63 g (0.022 moo 2,6-diethyl-2,3,6-trimethyl-4-oxypropylpiperidine-1-oxyl are reacted with t-butylperoxide in ethylbenzene. 6.1 g (77%) 1-(1-phenylethoxy)-2,6-diethyl-2,3,6-trimethyl-4-hydroxypiperidine are obtained as yellowish liquid.

EXAMPLE 9

1-t-butyloxy-2,6-diethyl-2,3,6-trimethyl-4-oxopiperidine (No. 104)

The title compound is prepared in analogy to example 6. 4.77 g (0.022 mol) 2,6-diethyl-2,3,6-trimethyl-4-oxypropylpiperidine-1-oxy and 2.13 g (0.015 mol) 2,2'-azobis(2-methyl-propane) are reacted in ethylbenzene. 1.15 g 1-t-butyloxy-2,6-diethyl-2,3,6-trimethyl-4-oxypiperidine are obtained as yellowish liquid.

Elemental analysis calculated for $C_{16}H_{31}NO_2$: C, 71.33%; H, 11.60%; N, 5,20%. Found: C, 71,28%; H, 11.67%; N, 5.45%.

EXAMPLE 10

1-(1-phenylethoxy)-2,6-dipropyl-2-ethyl-2,6-dimethyl-4-oxypiperidine (No. 105)

The title compound is prepared in analogy to example 6. 5.0 g (0.021 mol) 2,6-Dipropyl-2-ethyl-2.6-dimethyl-4-oxopiperidine-1-oxyl and t-butylperoxide are reacted In ethylbenzene. 3.4 g (49%) 1-(1-phenylethoxy)-2,6-dipropyl-2-ethyl-2,6-dimethyl-4-oxypiperidine are obtained as yellowish liquid.

Elemental analysis calculated for $C_{23}H_{37}NO_2$: C, 76.83%; H, 10.37%; N, 3.90%. Found: C, 77.51%; H, 10.49%; N, 3.10%.

EXAMPLE 11

1-(1-phenylethoxy)-2,6-dipropyl-2-ethyl-2,6-dimethyl-4-hydroxy-piperidine Nr.106)

The title compound is prepared in analogy to example 1. 3.1 g (0.009 mol) 1-(1-phenylethoxy)-2,6-dipropyl-2-ethyl-2,6-dimethyl-4-oxypiperidine is reduced with sodium-borohydride in ethanol. 2.9 g (93 %) 1-(1-phenylethoxy)-2,6-dipropyl-2-ethyl-2.6-dimethyl-4-hydroxypiperidine are obtained as yellowish liquid.

Elemental analysis calculated for $C_{23}H_{39}NO_2$: C, 76.40%; H, 10.87%; N, 3.87%. Found: C, 75.89%; H, 11.14%; N, 3.18%.

EXAMPLE 12

2,2,6-trimethyl-6-ethyl-piperidine 33.8 g (02 mol) 2,2,6-trimethyl-6-ethyl-4-oxopiperidine, 14 g (0.28 mol) hydrazinhydrate and 13 g KOH in 80 ml diethylenglykol are stirred for 4 h at 160° C. Subsequently an aciditional amount of 30 g KOH dissolved In 30 ml water are acided. 30 ml are distilled off. To the residue two times 40 ml of water are acided and removed by distillation. The combined distillates are saturated with solid $K_2CO_3$ and extracted with methyl-tert.-butylether. From the extracts 6 g ( 19%) 2,2,6-trimethyl-6-ethyl-piperidine are isolated by fractionated distillation. A colorless liquid is obtained with a b. p. of 78-88° C./15 mbar.

$^1$H-NMR (CDCl$_3$), β ppm: 1.8-1.2 m (4×CH$_2$), 1.14 s (CH$_3$), 1.1 s (CH$_3$), 1.05 s (CH$_3$), 0.86 t (CH$_3$).

EXAMPLE 13

2,2,6-Trimethyl-6-ethyl-piperidine-1-oxyl

To a solution of 5.7 g (0.037 mol) 2,2,6-trimethyl-6-ethylpiperidine in 20 ml methanol, 0.07 g sodium wolframate and 10 ml of 30% hydrogen peroxide are acided. The mixture is stirred for 23 h at room temperature, diluted with a saturated NaCl solution and extracted with methyl-tert-butylether. The combined extracts are dried over $MgSO_4$ and concentrated under vacuum. The residue is subjected to column chromatography (silica gel, hexane-ethylacetate 9:1). 4.6 g (73%) pure 2,2,6-trimethyl-6-ethyl-1-oxyl are isolated as red oil.

Elemental analysis calculated for $C_{10}H_{20}NO$: C, 70.54%; H, 11.84%; N, 8.23%. Found: C, 70.18%; H, 12.02%; N, 8.20%.

EXAMPLE 14

1-(Dimethylcyanomethyloxy)-2,2,6-trimethyl-6-ethyl-piperidine (No 107)

A solution of 2.8 g (0.016 mol) 2,2,6-trimethyl-6-ethyl-piperidine-1-oxyl and 2.05 g (0.012 mol) azoisobutyronitril (AIBN) in 7 ml benzene are refluxed under argon atmosphere for 4 hours. Subsequently aciditional 1.5 g (0.009 mol) AIBN are acided and the mixture is heated for one hour under argon. The colorless solution is concentrated under vacuum and subjected to column chromatography (silica gel, hexane-ethylacetate 19:1). 1.63 g (42%) 1-(dimethylcyanomethyloxy)-2,2,6-trimethyl-6-ethyl-piperidine are isolated as colorless oil which slowly crystallizes to a solid with m. p. of 41-52° C.

Elemental analysis calculated for $C_{14}H_{26}N_2O$: C, 70.54%; H, 10.99%; N, 11.75%. Found: C, 70.49%; H, 10.71 %; N, 11.60%.

EXAMPLE 15

2,2,6-Trimethyl-6-ethyl-4-hydroxypiperidine-1-oxyl

To a solution of 27.2 g (0.16 mol) 2,2,6-trimethyl-6-ethyl-4-oxopiperidine in 100 ml methanol 3 g (0.08 mol) sodium borohydride are acided In portions. The temperature is kept below 30° C. After stirring over night 55 ml (0.64 mol) of 35% hydrogen peroxide, 0.5 g sodium tungstate, 40 ml of 20% sodium carbonate and aciditional 60 ml methanol are acided. After stirring for another 20 h at room temperature the reaction mixture is filtered, diluted with 100 ml saturated NaCl solution and subsequently extracted 3-times with hexane-methyl-tert-butylether (1:1). The combined extracts are dried over $MgSO_4$ and concentrated under vacuum. The residue is subjected to column chromatography (silica gel, hexane-ethylacetate 1:1). 12.5 g (42%) pure 2,2,6-trimethyl-6-ethyl-4-hydroxypiperidine-1-oxyl are isolated as red oil Elemental analysis calculated for $C_{10}H_{20}NO_2$: C, 64.48%; H, 10.82%; N, 7.52%. Found: C, 63.73%; H, 10.87%; N, 7.24%.

EXAMPLE 16

1-(dimethylcyanomethyloxy)-2,2,6-trimethyl-6-ethyl-4-hydroxypiperidine (No. 108)

A solution of 2.0 g (0.0107 mol) 2,2,6-trimethyl-6-ethyl-4-hydroxypiperidine-1-oxyl and 2.65 g (0.016 mol) azoisobutyronitril (AIBN) in 8 ml benzene is refluxed under argon for 30 minutes. The colorless solution is concentrated under vacuum and subjected to column chromatography (silica gel, hexane-ethylacetate 2:1). The combined fractions are recrystallized from hexane. 2.0 g (73%) 1-(dimethylcyanomethyloxy)-2,2,6-trimethyl-6-ethyl-4-hydroxypiperidine with a m. p. of 48-60° C. are isolated.

Elemental analysis calculated for $C_{14}H_{26}N_2O_2$: C, 66.11%; H, 10.30%; N, 11.01%. Found: C, 65.77%; H, 10.49%; N, 11.04%.

EXAMPLE 17

1-(1-phenylethoxy)-2,2,6-trimethyl-6-ethyl-4-hydroxypiperidine (No 109)

3.1 g (0.0166 mol) 2,2,6-trimethyl-6-ethyl-4-hydroxypiperidine-1-oxyl, 2.2 g (0.0153 mol) Copper (I) bromide and 4.1 g (0.0153 mol) 4,4'-di-.tert.-butyl-[2,2']bipyridinyl are acided to 20 ml benzene. The solution is purged with argon and evacuated for several times to remove the oxygen from the solution. With a syringe 2.79 g (0.0151 mol) 1-phenylethylbromide are acided. The mixture is stirred for 21 h at room temperature. The green suspension is filtered over Cellit and the filtrate is removed from benzene under vacuum. The residue is subjected to column chromatography (silica gel, hexane-ethylacetate 4:1). 2.18 g (45%) 1-(1-phenylethoxy)-2,2,6-trimethyl-6-ethyl-4-hydroxypiperidine are obtained as colorless oil.

Recrystallization from hexane results In crystals of a m. p. of 58-69° C. $^1$H-NMR ($CDCl_3$), β ppm: 7.3 m 5 H (ArH), 4.75 m 1H ($OCH(CH_3)Ph$), 3.88 m 1H (CHOH), 2.1-0.5 m 21H ($4 \times CH_3$, $1 \times C_2H_5$, $CH_2COCH_2$).

EXAMPLE 18

2,2,6-Trimethyl-6-isopropyl-4-oxopiperidine

The title compound is prepared In analogy to F. Asinger, M. Thiel, H. Baltz.: Monatshefte für Chemie 88, 464 (1957) from mesityloxide, methylisopropylketone and ammonia. A colorless liquid is obtained.

$^1$H-NMR ($CDCl_3$), β ppm: 2.25 m 4H ($CH_2COCH_2$), 1.64 m 1H ($CH(CH_3)_2$) 1,24 s ($CH_3$), 1.21 s (CH3), 1.07 s (CH3). 0.91 dd 6H ($CH(CH_3)_2$).

EXAMPLE 19

2,2,6-trimethyl-6-isopropyl-4-oxopiperidine-1-oxyl 2.75 g (0.015 mol) 2,2,6-trimethyl-6-isopropyl-4-oxopiperidine, 0.08 g sodium wolframate, 0.2 g sodium carbonate, 10 ml of 30% hydrogen peroxide and 10 ml methanol are stirred for 22 h at room temperature. 20 ml saturated NaCl solution are acided and the mixture is extracted 3-times with hexane-methyl-tert.-butylether (1:1). The combined extracts are dried over $MgSO_4$ and concentrated under vacuum. The residue is subjected to column chromatography (silica gel, hexane-ethylacetate 4:1). 1.8 g (60%) pure 2,2,6-trimethyl-6-isopropyl-4-oxopiperidine are isolated as red oil. Recrystallization from pentane results in a solid of a m. p. of 47-53° C.

Elemental analysis calculated for $C_{11}H_{20}NO_2$: C, 66.63%; H, 10.17%; N, 7.06%. Found: C, 66.42%; H, 10.19%; N, 7.10%.

EXAMPLE 20

1-(dimethylcyanomethyl)-2,2,6-trimethyl-6-isopropyl-4-oxopiperidine (No 111)

A solution of 1.0 g (0.005 mol) 2,2,6-trimethyl-6-isopropyl-4-oxopiperidine-1-oxyl and 1.6 g (0.01 mol) azoisobutyronitril (AIBN) in 5 ml benzene are refluxed under argon for 30 minutes. The colorless solution is concentrated under vacuum and subjected to column chromatography (silica gel, hexane-ethylacetate 9:1). The combined fractions are recrystallized from hexane. 0.55 g (41%) 1-(dimethylcyanomethyloxy)-2,2,6-trimethyl-6-isopropyl-4-oxopiperidine with a m. p. of 32-44° C. are obtained.

$^1$H-NMR ($CDCl_3$), β ppm: 2.5 m 4H ($CH_2COCH_2$), 2.15 m 1H ($CH(CH_3)_2$), 1.69 s 6H (($CH_3)_2CCN$), 1.37 s (CH3),1.33 s (CH3), 1.26 s (CH3), 0.91 dd 6H ($CH(CH_3)_2$).

EXAMPLE 21

2,2-dimethyl-6,6-diethyl-4-hydroxypiperidine

To a solution of 15.8 g (0.086 mol) 2,2-dimethyl-6,6-diethyl-4-oxopiperidine In 50 ml methanol 2.2 g (0.06 M) sodium borohydride are acided in portions. The temperature is kept below 30° C. After stirring over night methanol is removed under vacuum and the residue is diluted with 20 ml 2N-NaOH. The solution is extracted with ethylacetate. The combined extracts are washed with saturated NaCl solution, dried over MgSO$_4$ and dried under vacuum at 60° C./50 mbar until a constant weight is achieved. 15.8 g (99%) 2,2-dimethyl-6,6-diethyl-4-hydroxypiperidine are obtained as yellowish oil. :

EXAMPLE 22

2,2-dimethyl-6,6-diethyl-4-hydroxypiperidine-1-oxyl 15.85 g (0.085 mol) 2,2-dimethyl-6,6-diethyl-4-hydroxypiperidine, 0.25 g sodium wolframate, 1 g sodium carbonate, 26 ml of 35% hydrogen peroxide and 45 ml methanol are stirred for 28 h at room temperature. 100 ml saturated NaCl solution are acided and the mixture is extracted 3-times with hexane-methyl-tert.-butylether (1:1). The combined extracts are dried over MgSO$_4$ and concentrated under vacuum. The residue is subjected to column chromatography (silica gel, hexane- ethylacetate 2:1). 8.55 g (50%) pure 2,2-Dimethyl-6,6-diethyl-4-hydroxypiperidine-1-oxyl are isolated as red oil.

EXAMPLE 23

1-(1-phenylethoxy)-2,2-dimethyl-6,6-diethyl-4-hydroxypiperidine. (No 110)

2.0 g (0.01 mol) 2,2-dimethyl-6,6-diethylhydroxypiperidine-1-oxyl, 1.43 g (0.01 mol) Copper (I) bromide and 1.56 g (0.01 mol) 4,4'-di-.tert.-butyl-[2,2']bipyridinyl are acided to 20 ml benzene. The solution is purged with argon and evacuated for several times to remove the oxygen from the solution. With a syringe 1.85 g (0.01 mol) 1-phenylethylbromide are acided. The mixture is stirred for 16 h at room temperature. Aciditional 0.3 g (0.002 mol Copper (I) are acided under argon and the solution is stirred for another 23 h. The green suspension is filtered over Cellit and the filtrate is removed from benzene under vacuum. The residue is subjected to column chromatography (silica gel, hexane-ethylacetate 3:1). After recrystallization from hexane 0.8 g 1-(1-phenylethoxy)-2,2-dimethyl-6,6-diethyl-4-hydroxypiperidine with a m. p. of 84-86° C. are obtained.

Elemental analysis calculated for C$_{19}$H$_{31}$NO$_2$: C, 74.71%; H, 10.23%; N, 4.59%. Found: C, 74.77%; H, 10.39%; N, 4.55%.

EXAMPLE 24

1-(1-phenylethoxy)-2,3,6-trimethyl-2,6-diethyl-4-oxopiperidine (Nr 112)

The title compound is prepared in analogy to example 6. 4.7 g (0.022 mol) 2,6-diethyl-2,3,6-trimethyl-4-oxypiperidine-1-oxyl are reacted with t-butylperoxide in ethylbenzene. 5.0 g (71%) 1-(1-phenylethoxy)-2,6-dipropyl-2-ethyl-6-dimethyl-4-oxypiperidine are obtained as yellowish liquid.

Elemental analysis calculated for C$_{20}$H$_{31}$NO$_2$: C, 75.67%; H, 9.84%; N, 4.41%. Found: C, 75.60%; H, 9.77%; N, 4.34%.

EXAMPLE 25

1-(1-phenylethoxy)-2,2-dimethyl-6,6-diethyl-4-benzoyloxypiperidine (No 113)

A) 2,2-Dimethyl-6,6-diethyl-4-benzoyloxypiperidine-1-oxyl

To a stirred solution of 6.05 g (0.03 mol) of 2,2-dimethyl-6,6-diethyl-4-hydroxypiperidine-1-oxyl in 20 ml of pyridine are slowly and under cooling with ice acided 3.8 ml (0.032 mol) of benzoylchloride. Afterwards, the mixture is stirred for 3.5 h at room temperature, then diluted with 200 ml of water and extracted twice with 50 ml of hexane. The combined extracts are washed with water, dried over MgSO$_4$ and evaporated In vacuo to give 9.1 g of 2,2-dimethyl-6,6-diethyl-4-hydroxypiperidine-1-oxyl as a thick, red oil.

Elemental analysis calculated for C$_{18}$H$_{26}$N$_3$: C, 71.02%; H, 8.61 %; N, 4.60%. Found: C, 70.96%; H, 8.76%; N, 4.53%.

B) 3.04 g (0.01 mol) of 2,2-dimethyl-6,6-diethyl-4-benzoyloxypiperidine-1-oxyl and 7.37 ml of t-butylperoxide in 200 ml of ethylbenzene are photolyzed as described In example 6 to afford 5.5 g of 1-(1-phenylethoxy)-2,2-dimethyl-6,6-diethyl-4-benzoyloxypiperidine as a thick colorless oil.

$^1$H-NMR (CDCl$_3$), d ppm: 0.5-2.0 m (23H), 4.74 m (1H), 5.2 m (1H), 7.2-7.6 m (8 H), 8.00-8.03 d (2 H).

EXAMPLE 26

2,6-diethyl-2,3,6-trimethyl-4-lauroyloxypiperidine-1-oxyl

To a stirred solution of 21,4 g (0.1 mol) of 2,6-diethyl-2,3,6-trimethyl-4-hydroxypiperidine-1-oxyl in 15 ml triethylamine and 70 ml toluene are slowly and under cooling with ice acided 19.9 g (0.091 mol) of lauroyl chloride. Afterwards, the mixture is stirred for 6 hrs at room temperature, then diluted with 200 ml of water and extracted twice with 100 ml of toluene. The combined extracts are washed with water, dried over MgSO$_4$ and evaporated In vacuo and the residue is subjected to column chromatography (silicagel, hexane-ethylacetate (5:1)). 25,2 g (64%) 2,6-diethyl-2,3,6-trimethyl-4-lauroyloxypiperidine-1-oxyl are isolated as A red oil.

Elemental analysis calculated for C$_{24}$H$_{46}$NO$_3$: C, 72.67%; H, 11.69%; N, 3.53%. Found: C, 72.39%; H, 11.60%; N, 3.30%.

EXAMPLE 27

2,6-diethyl-2,3,6-trimethyl-4-stearoyloxypiperidine-1-oxyl

To a stirred solution of 5 g (0.023 mol) of 2,6-diethyl-2,3,6-trimethyl-4-hydroxypiperidine-1-oxyl in 5 ml triethylamine and 40 ml toluene are slowly and under cooling with Ice acided 7,1 g (0.021 mol) of stearyl chloride. Afterwards, the mixture is stirred for 6 hrs at room temperature, then diluted with 100 ml of water and extracted twice with 50 ml of toluene . The combined extracts are washed with water, dried over MgSO$_4$ and evaporated in vacuo and the residue is subjected to column chromatography (silicagel, hexane-ethylacetate (5:1)). 5,8 g (52%) 2,6-diethyl-2,3,6-trimethyl-4-stearoyloxypiperidine-1-oxyl are isolated as a red oll.

Elemental analysis calculated for C$_{30}$H$_{58}$NO$_3$: C, 74.94%; H, 12.16%; N, 2.91%. Found: C, 74.96%; H, 12.00%; N, 2.69%.

EXAMPLE 28

2,2-dimethyl-6,6-diethyl-4-lauroyloxypiperidine-1-oxyl

To a stirred solution of 2,0 g (0.01 mol) of 2,2-dimethyl-6,6-diethyl-4-hydroxypiperidine-1-oxyl in 2 ml triethylamine and 25 ml toluene are slowly and under cooling with ice acided 2,0 g (0.0091 mol) of lauroyl chloride. Afterwards, the mixture is stirred for 6 hrs at room temperature, then diluted with 50 ml of water and extracted twice with 25 ml of toluene. The combined extracts are washed with water, dried over MgSO$_4$ and evaporated In vacuo and the residue is subjected to column chromatography (silicagel, hexane-ethylacetate (5:1)). 1,8 g (48%) 2,2-dimethyl-6,6-diethyl-4-lauroyloxypiperidine-1-oxyl are isolated as a red oil.

Elemental analysis calculated for C$_{23}$H$_{44}$NO$_3$: C, 72.20%; H, 11.60%; N, 3.66%. Found: C, 72.01%; H, 11.61%; N, 3.48%.

EXAMPLE 29

2,2-dimethyl-6,6-diethyl-4-stearoyloxypiperidine-1-oxyl

To a stirred solution of 5,09 (0.025 mol) of 2,2-dimethyl-6,6-diethyl-4-hydroxypiperidine-1-oxyl in 5 ml triethylamine and 40 ml toluene are slowly and under cooling with Ice acided 7,9 g (0.023 mol) of stearoyl chloride. Afterwards, the mixture is stirred for 6 hrs at room temperature, then diluted with 100 ml of water and extracted twice with 50 ml of toluene. The combined extracts are washed with water, dried over MgSO$_4$ and evaporated in vacuo and the residue is subjected to column chromatography (silicagel, hexane-ethylacetate (5:1)). 6,15 g (52%) 2,2-dimethyl-6,6-diaethyl-4-stearoyloxypiperidine-1-oxyl are isolated as a red oil.

Elemental analysis calculated for C$_{29}$H$_{56}$NO$_3$: C, 74.62%; H, 12.09%; N, 3.00%. Found: C, 74.47%; H, 12.03%; N, 2.99%.

EXAMPLE 30

2,6-diethyl-2,3,6-trimethyl-4-propoxypiperidine-1-oxyl

To a stirred solution of 128 g (0.6 mol) of 2,6-diethyl-2,3,6-trimethyl-4-hydroxypiperidine-1-oxyl, 80 g NaOH, 80 g water, 19,3 g tetrabutylammonium bromide and 240 ml toluene are slowly acided at 50° C. 111 g (0.9 mol) of propylbromide. Afterwards, the mixture is stirred for 10 hrs at 50° C. then diluted with 200 ml of water and the organic phase is separated. The organic phase is washed with water, dried over MgSO$_4$ and evaporated in vacuo. The raw product is purified by distillation. 81 g (54%) 2,6-diethyl-2,3,6-trimethyl-4-propoxypiperidine-1-oxyl are isolated as a red oil.

Elemental analysis calculated for C$_{15}$H$_{30}$NO$_2$: C, 70.27%; H, 11.79%; N, 5.46%. Found: C, 70.26%; H, 11.88%; N, 5.40%.

The N—O—X compounds prepared, are listed in Table 1

TABLE 1

| No. | Compound |
| --- | --- |
| 101 | |
| 102 | |
| 103 | |
| 104 | |
| 105 | |
| 106 | |
| 107 | |
| 108 | |
| 109 | |
| 110 | |

TABLE 1-continued

| No. | Compound |
|---|---|
| 111 | (structure: piperidine with N—O—C(CH3)2—CN, ethyl and methyl substituents, ketone) |
| 112 | (structure: piperidine with N—O—CH(CH3)—phenyl, ethyl and methyl substituents, ketone) |
| 113 | (structure: benzoate ester of piperidine with N—O—CH(CH3)—phenyl, ethyl and methyl substituents) |

B) Polymerizations using compounds of Table 1 or their N—O• precursors as initiators General remarks:

Solvents and monomers are distilled over a Vigreux column under argon atmosphere or under vacuum, shortly before being used.

To remove oxygen all polymerization reaction mixtures are flushed before polymerization with argon and evacuated under vacuum applying a freeze-thaw cycle. The reaction mixtures are then polymerized under argon atmosphere.

At the start of the polymerization reaction, all starting materials are homogeneously dissolved.

Conversion is determined by removing unreacted monomers from the polymer at 80° C. and 0.002 torr for 30 minutes weighing the remaining polymer and subtract the weight of the initiator.

Characterization of the polymers is carried out by MALDI-MS (Matrix Assisted Laser Desorption Ionization Mass Spectrometry) and/or GPC (Gel Permeation Chromatography).

MALDI-MS: Measurements are performed on a linear TOF (Time Of Right) MALDI-MS LDI-1700 Linear Scientific Inc., Reno, USA. The matrix is 2,5-dihydroxybenzoic acid and the laser wavelength is 337 nm.

GPC: is performed using RHEOS 4000 of FLUX INSTRUMENTS. Tetrahydrofurane (THF) is used as a solvent and is pumped at 1 ml/min. Two chromatography columns are put In series: type Plgel 5 μm mixed-C of POLYMER INSTRUMENTS, Shropshire, UK. Measurements are performed at 40° C. The columns are calibrated with low polydispersity polystyrenes having Mn from 200 to 2000000 Dalton. Detection is carried out using a RI-Detector ERC-7515A of ERCATECH AG at 30° C.

B) Polymerizations with Acrylates

B1-B10 Homopolymers

EXAMPLE B1

Polymerization of n-butylacrylate using compound 101

In a 50 ml three neck flask, equipped with thermometer, cooler and magnetic stirrer, 710,mg (2.34 mmol) of compound 101 and 20 g (156 mmol) of n-butylacrylate are mixed and degased. The clear solution obtained is heated under argon to 145° C. and polymerization is carried out during 5 h. The reaction mixture is then cooled to 80° C. The remaining monomer is removed by evaporation under high vacuum. 19.3 g (93%) of the Initial monomer have reacted. A clear colorless viscous fluid is obtained.

GPC: Mn=12000, Mw=21300, Polydispersity (PD)=1.77

EXAMPLE B2

Polymerization of n-butylacrylate using compound 102

In a 50 ml three neck flask, equipped with thermometer, cooler and magnetic stirrer, 743 mg (2.34 mmol) of compound 102 and 20 g (156 mmol) of n-butylacrylate are mixed and degased. The clear solution obtained is heated under argon to 145° C. and polymerization is carried out during 5 h. The reaction mixture is then cooled to 80° C. The remaining monomer is removed by evaporation under high vacuum. 16.8 g (80%) of the initial monomer have reacted. A clear colorless viscous fluid is obtained.

GPC: Mn=7500, Mw=8700, Polydispersity (PD)=1.16

EXAMPLE B3

Polymerization of n-butylacrylate using compound 103

In a 50 ml three neck flask, equipped with thermometer, cooler and magnetic stirrer, 4.51 g (12.5 mmol) of compound 103 and 16 g (125 mmol) of n-butylacrylate are mixed and degased. The clear solution obtained is heated under argon to 145° C. and polymerization is carried out during 5 h. The reaction mixture is then cooled to 80° C. The remaining monomer is removed by evaporation under high vacuum. 14.9 g (65%) of the Initial monomer have reacted. A dear orange viscous fluid is obtained. The raw product is is subjected to column chromatography (silica gel, hexane-ethylacetate 1:4) and 10.4 g of a colorless viscous liquid is obtained.

GPC: Mn=1550, Mw=1900, Polydispersity(PD)=1.22

EXAMPLE B4

Polymerization of n-butylacrylate using compound 104

In a 50 ml three neck flask, equipped with thermometer, cooler and magnetic stirrer, 473 mg (1.76 mmol) Nr 104 and 15 g (117 mmol) of n-butylacrylate are mixed and degased. The clear solution obtained is heated under argon to 145° C. and polymerization is carried out during 5 h. The reaction mixture is then cooled to 80° C. The remaining monomer is removed by evaporation under high vacuum. 1.65 g (11%) of the initial monomer have reacted. A clear slight orange viscous fluid is obtained.

EXAMPLE B5

Polymerization of n-butylacrylate using compound 106

In a 50 ml three neck flask, equipped with thermometer, cooler and magnetic stirrer, 844 mg (2.34 mmol) of compound 106 and 20 g (156 mmol) of n-butylacrylate are mixed and degased. The clear solution obtained is heated under argon to 145° C. and polymerization is carried out during 2 h. The reaction mixture is then cooled to 80° C. The remaining monomer is removed by evaporation under high vacuum. 16.8 g (80%) of the initial monomer have reacted. A dear colorless viscous fluid is obtained.

After 2 h 15.2 g (76%) of the initial monomer have reacted. A clear colorless viscous fluid is obtained.

GPC: Mn=6550, Mw=8100, Polydispersity (PD)=1.24

EXAMPLE B6

Polymerization of n-butylacrylate using compound 110

In a 50 ml three neck flask, equipped with thermometer, cooler and magnetic stirrer, 357 mg (1.2 mmol) of compound 110 and 10 g (78 mmol) of n-butylacrylate are mixed and degased. The clear solution obtained is heated under argon to 145° C. and polymerization is carried out during 5 h. The reaction mixture is then cooled to 80° C. The remaining monomer is removed by evaporation under high vacuum. 7.6 g (76%) of the initial monomer have reacted. A dear slightly orange viscous fluid is obtained.

GPC: Mn=6100, Mw=7500, Polydispersität (PD)=1.2

EXAMPLE B7

Polymerization of n-butylacrylate using compound 112

In a 50 ml three neck flask, equipped with thermometer, cooler and magnetic stirrer, 743 mg (2.34 mmol) of compound 112 and 20 g (156 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 16g (80%) of the initial monomer have reacted. A clear slightly orange viscous fluid is obtained.

GPC: Mn=7500, Mw=8700, Polydispersität (PD)=1.2
MALDI-TOF: Mn=6400, Mw=7700, Polydispersität (PD)=1.2

EXAMPLE B8

Polymerization of dimethylaminoethylacrylate using compound 102

A 50 ml round-bottom three necked flask, equipped with thermometer, condenser and magnetic stirrer is charged with 0.268 g (0.8 mmol) of compound 102 and 8 g (56 mmol) of dimethylaminoethylacrylate and degassed. The clear yellow solution is then heated to 145° C. under argon. The mixture is stirred for 1 hour at 145° C. and then cooled to 60° C. and the remaining monomer is evaporated under high vacuum. 5.6 g (70%) of a brown viscous polymer are obtained.

GPC: Mn=2300, Mw=3700, Polydispersity=1.6

EXAMPLE B9

Polymerization of dimethylaminoethylacrylate using compound 110

A 50 ml round-bottom three necked flask, equipped with thermometer, condenser and magnetic stirrer is charged with 0.256 g (0.8 mmol) of compound 110 and 8 g (56 mmol) of dimethylaminoethylacrylate and degassed. The clear yellow solution is then heated to 145° C. under argon. The mixture is stirred for 1 hour at 145° C. and then cooled to 60° C. and the remaining monomer is evaporated under high vacuum. 5.7 g (72%) of a brown viscous. polymer are obtained.

GPC: Mn=2100, Mw=3300, Polydispersity=1.6

EXAMPLE B10

Polymerization of t-butylacrylate using compound 110

A round-bottom three necked flask equipped with thermometer, condenser and magnetic stirrer is charged with 0.178 g (0.6 mmol) of compound 110 and 5 g (39 mmol) of t-butylacrylate and degassed. The clear solution is then heated to 145° C. under argon. The mixture is stirred for 3 hour at 145° C. and then cooled to 60° C. and the remaining monomer is evaporated under high vacuum. 1 g (20%) of a brown viscous polymer are obtained.

GPC: Mn=1800, Mw=2900, Polydispersity=1.6

B11-B15 Blockcopolymers

EXAMPLE B11

Copolymerization of poly-n-butylacrylate made with compound 102 with n-butylacrylate A round-bottom three necked flask, equipped with thermometer, condenser and magnetic stirrer is charged with 12 g (93 mmol) n-butylacrylate and 12.5 g of poly-n-butylacrylate (made with compound 102, Mn=7500, PD=1.2) and degassed. The solution is then heated to 145° C. under argon. The mixture is stirred for 5 hour at 145° C. and then cooled to 60° C. and the remaining monomer is evaporated under high vacuum. 20% of the aciditional lmonomer is reacted and an orange viscous liquid is obtained.

GPC: Mn=8500, Mw=11400, Polydispersity=1.4

EXAMPLE B12

Copolymerization of poly-n-butylacrylate made with compound 102 with dimethylaminoethylmethacrylate A round-bottom three necked flask, equipped with thermometer, condenser and magnetic stirrer is charged with 14.5 9 (93 mmol) dimethylaminoethylmethacrylate and 12.5 g of poly-n-butylacrylate (made with compound 102, Mn=7500, PD=1.2) and degassed. The solution is then heated to 145° C. under argon. The mixture is stirred for 5 hour at 145° C. and then cooled to 60° C. and the remaining monomer is evaporated under high vacuum. 10% of the aciditional monomer is reacted and an orange viscous liquid is obtained.

GPC: Mn=8200, Mw=13200, Polydispersity=1.6

EXAMPLE B13

Copolymerization of poly-n-butylacrylate made with compound 110 with n-butylacrylate A round-bottom three necked flask, equipped with thermometer, condenser and magnetic stirrer is charged with 11 g (86 mmol) n-butylacrylate and 11.5 g of poly-n-butylacrylate (made with compound 110, Mn=5600, PD=1.3) and degassed. The solution is then heated to 145° C. under argon. The mixture is stirred for 5 hour at 145° C. and then cooled to 60° C. and the remaining monomer is evaporated under high vacuum. 10% of the acidional monomer is reacted and an orange viscous liquid is obtained.
GPC: Mn=6500, Mw=8500, Polydispersity=1.3

EXAMPLE B14

Copolymerization of poly-n-butylacrylate made with compound 110 with dimethylaminoethylmethacrylate (50/50)

A round-bottom three necked flask, equipped with thermometer, condenser and magnetic stirrer is charged with 5 9 (37 mmol) dimethylaminoethylmethacrylate and 5 g of poly-n-butylacrylate (made with compound 110, Mn=5600, PD=1.3) and degassed. The solution is then heated to 145° C. under argon. The mixture is stirred for 3 hour at 145° C. and then cooled to 60° C. and the remaining monomer is evaporated under high vacuum. 20% of the acidional monomer is reacted and an orange viscous liquid is obtained.
GPC: Mn=5500, Mw=7400, Polydispersity=1.3

EXAMPLE B15

Copolymerization of poly-n-butylacrylate made with compound 110 with dimethylaminoethylmethacrylate (20/80)

A round-bottom three necked flask, equipped with thermometer, condenser and magnetic stirrer is charged with 18 g (115 mmol) dimethylaminoethylmethacrylate and 4 g of poly-n-butylacrylate (made with compound 110, Mn=5600, PD=1.3) and degassed. The solution is then heated to 145° C. under argon. The mixture is stirred for 3 hour at 145° C. and then cooled to 60° C. and the remaining monomer is evaporated under. high vacuum. 30% of the acidional monomer is reacted and an orange viscous liquid is obtained.
GPC: Mn=10000, Mw=17700, Polydispersity=1.8

C) Polymerizations with Styrene

Homopolymerization with NOR

EXAMPLE C1

Polymerization of styrene using compound 102

50 ml of styrene and 0.087 mol/l of compound 102 are heated under argon for 6 hrs to 130° C. The reaction mixture is then cooled to 80° C. and the remaining monomer is removed by evaporation under high vacuum. 33 g (66%) of a colorless polymer are obtained.
GPC:Mn=8000, Mw=9100, Polydispersity=1.14

EXAMPLE C2

Polymerization of styrene using compound 102

50 ml of styrene and 0,0087mol/l of compound 102 are heated under argon for 6 hrs to 130° C. The reaction mixture is then cooled to 80° C. and the remaining monomer is removed by evaporation under high vacuum. 37,5 g (75%) of a colorless polymer are obtained.
GPC: Mn=48400, Mw=67200, Polydispersity=1.39

Homopolymerization with nitroxide+benzoylperoxide (BPO)

EXAMPLE C3

Polymerization of styrene using nitroxide from Example A2+(BPO)

50 ml of styrene, 0,0087 mol/l nitroxide (from Example 2) and 0,0069 mol/l BPO are heated under argon for 6 hrs to 120° C. The reaction mixture is then cooled to 80° C. and the remaining monomer is removed by evaporation under high vacuum. 27,5 g (55%) of a colorless polymer are obtained.
GPC:Mn=48100, Mw=61500, Polydispersity=1.28

EXAMPLE C4

Polymerization of styrene using nitroxide from Example A2+BPO 100 ml of styrene, 0,087 mol/l nitroxide (from Example 2) and 0,069 mol/l BPO are heated under argon for 6 hrs to 120° C. The reaction mixture is then cooled to 80° C. and the remaining monomer is removed by evaporation under high vacuum. 35 g (35%) of a colorless polymer are obtained.
GPC: Mn=6200, Mw=7000, Polydispersity=1.13

EXAMPLE C5

Polymerization of styrene using nitroxide from Example A26+BPO 50 ml of styrene, 0.087 mol/l nitroxide (from Example 26) and 0.069 mol/l BPO are heated under argon for 6 hrs to 130° C. The reaction mixture is then cooled to 80° C. and the remaining monomer is removed by evaporation under high vacuum. 39 g (78%) of a colorless polymer are obtained.
GPC: Mn=9000, Mw=10600, Polydispersity=1.18

EXAMPLE C6

Polymerization of styrene using nitroxide from Example A26+BPO 50 ml of styrene, 0,0087 mol/l nitroxide (from Example 26) and 0,0069 mol/l BPO are heated under argon for 6 hrs to 130° C. The reaction mixture is then cooled to 80° C. and the remaining monomer is removed by evaporation under high vacuum. 40 g (80%) of a colorless polymer are obtained.
GPC: Mn=50600, Mw=72000, Polydispersity=1.43

EXAMPLE C7

Copolymerization Styrene/Styrene 5 ml of polystyrene from Example 4 and 5 g of styrene are heated under argon for 6 hrs to 130° C. The reaction mixture is then cooled to 80° C. and the remaining monomer is removed by evaporation under high vacuum. A colorless polymer is obtained.
GPC: Mn=9500, Mw=12000, Polydispersity=1.27

EXAMPLE C8

Copolymerization Styrene/n-Butylacrylate 5 ml of polystyrene from Example C4 and 5 g of n-butylacrylate are heated under argon for 6 hrs to 130° C. The reaction mixture is then cooled to 80° C. and the remaining monomer is removed by evaporation under high vacuum. A colorless polymer is obtained.

GPC: Mn=8200, Mw=9700, Polydispersity=1.18

The invention claimed is:

1. A polymerizable composition, comprising
a) at least one ethylenically unsaturated monomer or oligomer,
b) 1-oxy-polyalkyl-piperidine compound selected from the group consisting of

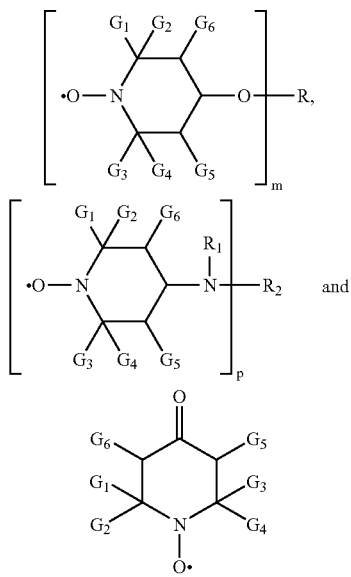

wherein $G_1$, $G_2$, $G_3$ and $G_4$ are independently alkyl of 1 to 4 carbon atoms with the proviso that at least one is not methyl or $G_1$ and $G_2$, or $G_3$ and $G_4$, or $G_1$ and $G_2$ and $G_3$ and $G_4$ together are pentamethylene;

$G_5$ and $G_6$ independently are hydrogen or $C_1$-$C_4$alkyl;

m is 1, 2, 3 or 4;

R, if m is 1, is hydrogen, $C_1$-$C_{18}$alkyl which is uninterrupted or $C_2$-$C_{18}$alkyl which is interrupted by one or more oxygen atoms, cyanoethyl, or phosphorus-containing acid or a monovalent silyl radical;

R, if m is 2, is $C_2$-$C_{12}$alkylene, $C_4$-$C_{12}$alkenylene, xylylene, a divalent radical of an aliphatic dicarboxylic acid having 2 to 36 carbon atoms, or a cycloaliphatic or aromatic dicarboxylic acid having 8-14 carbon atoms or of an aliphatic, cycloaliphatic or aromatic dicarbamic acid having 8-14 carbon atoms; or R is a divalent radical of a phosphorus-containing acid or a divalent silyl radical;

R, if m is 3, is a trivalent radical of an aliphatic, cycloaliphatic or aromatic tricarboxylic acid, R, if m is 4, is a tetravalent radical of an aliphatic, cycloaliphatic or aromatic tetracarboxylic acid;

p is 1;

$R_1$ is $C_1$-$C_{12}$alkyl, $C_5$-$C_7$cycloalkyl or benzoyl; and $R_2$ is $C_1$-$C_{18}$alkyl, $C_5$-$C_7$cycloalkyl or a group of the formula —CO-Z- wherein Z is hydrogen, methyl or phenyl; and c) a radical iniator X• capable of initiating polymerization of ethylenically unsaturated monomers.

2. A process for preparing an oligomer, a cooligomer, a polymer or a copolymer (block or random) by free radical polymerization of at least one ethylenically unsaturated monomer/oligomer, which comprises subjecting a composition according to claim 1 to heat or actinic radiation.

* * * * *